US010851086B2

(12) United States Patent
Li et al.

(10) Patent No.: US 10,851,086 B2
(45) Date of Patent: Dec. 1, 2020

(54) POLYCRYSTALLINE FORM OF DEHYDROPHENYLAHISTIN-LIKE COMPOUND, AND MANUFACTURING AND PURIFICATION METHOD AND APPLICATION THEREOF

(71) Applicant: MARINE BIOMEDICAL RESEARCH INSTITUTE OF QINGDAO CO., LTD., Shandong (CN)

(72) Inventors: Wenbao Li, Shandong (CN); Shixiao Wang, Shandong (CN); Zhongpeng Ding, Shandong (CN); Yingwei Hou, Shandong (CN); Huashi Guan, Shandong (CN)

(73) Assignee: MARINE BIOMEDICAL RESEARCH INSTITUTE OF QINGDAO CO., LTD., Shandong (CN)

( * ) Notice: Subject to any disclaimer, the term of this patent is extended or adjusted under 35 U.S.C. 154(b) by 0 days.

(21) Appl. No.: 16/325,166

(22) PCT Filed: Jul. 24, 2017

(86) PCT No.: PCT/CN2017/094066
§ 371 (c)(1),
(2) Date: Feb. 12, 2019

(87) PCT Pub. No.: WO2018/028420
PCT Pub. Date: Feb. 15, 2018

(65) Prior Publication Data
US 2019/0177302 A1  Jun. 13, 2019

(30) Foreign Application Priority Data

Aug. 12, 2016 (CN) .......................... 2016 1 0664088
Aug. 12, 2016 (CN) .......................... 2016 1 0664196
Aug. 12, 2016 (CN) .......................... 2016 1 0665377

(51) Int. Cl.
*C07D 403/06* (2006.01)
*A61P 35/00* (2006.01)
*A61K 31/496* (2006.01)
*A61P 31/10* (2006.01)

(52) U.S. Cl.
CPC .......... *C07D 403/06* (2013.01); *A61K 31/496* (2013.01); *A61P 31/10* (2018.01); *A61P 35/00* (2018.01); *C07B 2200/13* (2013.01)

(58) Field of Classification Search
CPC ........ C07D 403/06; A61P 31/10; A61P 35/00; A61K 31/496
USPC ...................................................... 544/385
See application file for complete search history.

(56) References Cited

U.S. PATENT DOCUMENTS

| 7,064,201 | B2 | 6/2006 | Hayashi et al. |
| 10,434,098 | B2* | 10/2019 | Li .......................... C07D 233/64 |
| 2007/0078138 | A1* | 4/2007 | Palladino ............. C07D 487/04 514/249 |
| 2008/0221122 | A1 | 9/2008 | Palladine et al. |
| 2012/0277251 | A1* | 11/2012 | Palladino ............. C07D 403/06 514/255.05 |
| 2018/0140600 | A1 | 5/2018 | Li et al. |
| 2018/0194749 | A1* | 7/2018 | Huang ................. B01D 9/0045 |

FOREIGN PATENT DOCUMENTS

| CN | 1684955 | A |  | 10/2005 |
| CN | 101633655 | A |  | 1/2010 |
| CN | 105348186 | A |  | 2/2016 |
| CN | 106279039 | A |  | 1/2017 |
| CN | 107286139 |  | * | 10/2017 |
| CN | 108026075 | A |  | 5/2018 |
| CN | 109498627 |  | * | 3/2019 |
| WO | 2001/053290 | A1 |  | 7/2001 |
| WO | 2004/054498 | A2 |  | 7/2004 |
| WO | 2005/077940 | A1 |  | 8/2005 |
| WO | 2007/035841 | A1 |  | 3/2007 |
| WO | 2012/035436 | A1 |  | 3/2012 |
| WO | 2016/192586 | A1 |  | 12/2016 |
| WO | 2017/011399 | A1 |  | 1/2017 |

OTHER PUBLICATIONS

Ding; Bioorganic & Medicinal Chemistry Letters 2017, 27, 1416-1419; with 11 pages of Supplementary Material. (Year: 2017).*
Ding; Molecular Diversity 2017, 21, 577-583. (Year: 2017).*
Ma; Bioorganic & Medicinal Chemistry 2018, 26, 4687-4692. (Year: 2018).*
Ma; Bioorganic & Medicinal Chemistry 2019, 27, 1836-1844. (Year: 2019).*
Millward; Invest New Drugs 30, 2012, 1065-1073. (Year: 2012).*
Translation of International Search Report and Written Opinion for Application No. PCT/CN2017/094066 dated Oct. 18, 2017 (12 pages).
International Search Report and Written Opinion for Application No. PCT/CN2016/083610 dated Aug. 19, 2016 (8 pages).

(Continued)

*Primary Examiner* — Daniel R Carcanague
(74) *Attorney, Agent, or Firm* — Michael Best & Friedrich LLP

(57) ABSTRACT

A polycrystalline form of a dehydrophenylahistin-like compound, and a manufacturing and purification method and application thereof. A (3Z,6Z)-3-benzylidene-6-[(5-tert-butyl-1H-imidazol-4-yl)deuteromethylene]piperazine-2,5-dione monohydrate crystal and a (3Z,6Z)-3-benzylidene-6-[(5-tert-butyl-1H-imidazol-4-yl)methylene]piperazine-2,5-dione monohydrate crystal are more competitive crystalline forms with stable quality. The manufacturing and purification method is simple and easy to operate, and can effectively control the generation of a trans-isomer contaminant to obtain a high purity product. The polycrystalline form of the dehydrophenylahistin-like compound has a certain value in an application for manufacturing an antitumor pharmaceutical product.

12 Claims, 11 Drawing Sheets

(56) References Cited

OTHER PUBLICATIONS

Yamazaki et al., "Synthesis and Structure-Activity Relationship Study of Antimicrotubule Agents Phenylahistin Derivatives with a Didehydropiperazine-2,5-dione Structure," Journal of Medical Chemistry, 2011, 55, 1056-1071.

* cited by examiner

POLYCRYSTALLINE FORM OF DEHYDROPHENYLAHISTIN-LIKE COMPOUND, AND MANUFACTURING AND PURIFICATION METHOD AND APPLICATION THEREOF

CROSS-REFERENCE TO RELATED APPLICATION(S)

This application is a national stage filing under 35 U.S.C. § 371 of International Application No. PCT/CN2017/094066, filed on Jul. 24, 2017, which application claims the benefit of Chinese Patent Application No. 201610664088.6, filed on Aug. 12, 2016, Chinese Patent Application No. 201610665377.8, filed on Aug. 12, 2016, and Chinese Patent Application No. 201610664196.3, filed on Aug. 12, 2016, the entire contents of each of which are fully incorporated herein by reference.

TECHNICAL FIELD

The present invention belongs to the field of pharmaceutical chemistry and relates to polymorphs of dehydrophenylahistin-like compounds and method for preparation and purification thereof and use thereof.

BACKGROUND (3Z,6Z)-3-benzylidene-6-[(5-tert-butyl-1H-imidazol-4-yl)methylene]piperazine-2,5-dione belongs to dehydrophenylahistin-like compounds and has a formula of:

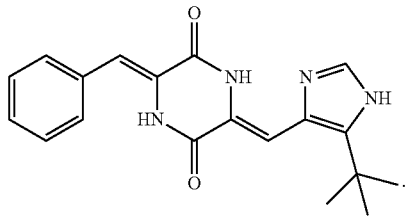 [SMILES: CC(C)(C)c1[nH]cnc1/C=c1\[nH]c(=O)/c(=C/c2ccccc2)[nH]c1=O]

Said compound is also known as Plinabulin (KPU-2, NPI-2358) and is developed by Nereus Pharmaceuticals Inc (US), and is a synthetic derivative of low molecular cyclodipeptide phenylahistin or halimide from marine *Aspergillus*, and is a tubulin-binding agent. Plinabulin can bind on the neighborhood of colchicine-binding site in tubulin and act on the cell to stop cell mitosis in its early stages which in turn induces cell death. At the same time, plinabulin also inhibits microtubule formation and migration of endothelial cells and MM cells, leading to dysfunction of tumor vasculature. Currently, plinabulin, as a drug candidate, has completed its Phase II clinical trials in the United States and is under Phase III clinical trials in China and the United States.

(3Z,6Z)-3-benzylidene-6-[(5-tert-butyl-1H-imidazol-4-yl)deuteromethylene]piperazine-2,5-dione belongs to deuterated dehydrophenylahistin-like compounds and has a formula of:

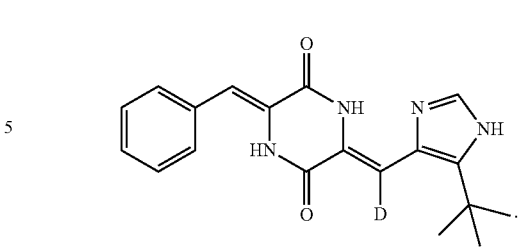

Said compound is a novel tubulin-binding agent obtained by structural modification using plinabulin as a lead compound. It has good antitumor activity and can overcome the drug tolerance of paclitaxel. It selectively acts on the neighborhood of colchicine-binding site in endothelial tubulin, inhibits the polymerization of tubulin, blocks off microtubule formation, stops cell mitosis in its early stages and thereby induces cell death. At the same time, said compound also inhibits neovascularization, blocks cancer cell feeding, and therefore synergistically inhibits rapid proliferation of cancer cells.

Studies show that the IC50 of (3Z,6Z)-3-benzylidene-6-[(5-tert-butyl-1H-imidazol-4-yl)deuteromethylene]piperazine-2,5-dione is lower than that of its analog plinabulin, but its water solubility is only 39.90 ng/mL, which seriously limits its clinical application. The inventors of the present invention has figured out the key techniques for preparing (3Z,6Z)-3-benzylidene-6-[(5-tert-butyl-1H-imidazol-4-yl)deuteromethylene]piperazine-2,5-dione through previous laborious work, for which a patent named Deuterated Dehydrophenylahistin-like Compounds And Preparation Method Thereof And Use Thereof In Preparation Of Anti-Tumor Drugs having a patent application number: 201510293269.8 has been filed for Chinese invention patent and PCT application.

Currently formulation of plinabulin applied for clinical trials is a concentrated injection solution with a solubility enhancer, being an injection, the quality and stability of plinabulin as a solid API are critically required, especially it is essential to obtain a crystalline form with high purity and good stability. Drug polymorphism is a common phenomenon in drug development. Different crystalline forms of the same drug molecule may have significant differences in appearance, melting point, solubility, dissolution rate, bioavailability, etc., which directly affect drug stability, bioavailability and therapeutic effects. Therefore, studying and screening plinabulin polymorphs are of great importance.

Currently there are no reports on the crystalline forms of (3Z,6Z)-3-benzylidene-6-[(5-tert-butyl-1H-imidazol-4-yl) deuteromethylene]piperazine-2,5-dione and their preparation methods.

At the same time, both (3Z,6Z)-3-benzylidene-6-[(5-tert-butyl-1H-imidazol-4-yl)methylene]piperazine-2,5-dione and deuterated dehydrophenylahistin-like compound (3Z,6Z)-3-benzylidene-6-[(5-tert-butyl-1H-imidazol-4-yl)deuteromethylene]piperazine-2,5-dione have strong photosensitivity, especially in solution, leading to the generation of isomers (3E,6Z)-3-benzylidene-6-[(5-tert-butyl-1H-imidazol-4-yl)methylene]piperazine-2,5-dione and (3E,6Z)-3-benzylidene-6-[(5-tert-butyl-1H-imidazol-4-yl)deuteromethylene]piperazine-2,5-dione during their preparation processes. As the above-mentioned isomers are not easy to be removed, it poses a problem for subsequent formulation and especially has impact on new drug application process as well as drug safety in clinical application. Therefore, preparation of (3Z,6Z)-3-benzylidene-6-[(5-tert-butyl-1H- imidazol-4-yl)methylene]piperazine-2,5-dione with high purity is of great significance. Moreover, currently reported methods for preparation and purification of (3Z,6Z)-3-benzylidene-6-[(5-tert-butyl-1H-imidazol-4-yl)methylene]piperazine-2,5-dione are complex, wherein purification of some intermediates through column chromatography limits its industrialized production, so it is of great importance to set up a suitable industrialized preparation method.

SUMMARY OF THE INVENTION

The object of the present invention is to provide polymorphs of dehydrophenylahistin-like compounds, method for preparation and purification thereof and use thereof.

In order to achieve said objects of the present invention, the following technical solutions are provided:

In one aspect, the present invention provides a crystalline form of (3Z,6Z)-3-benzylidene-6-[(5-tert-butyl-1H-imidazol-4-yl)deuteromethylene]piperazine-2,5-dione as shown in Formula (I), and said crystalline form has at least three X-ray powder diffraction characteristic peaks at 2θ diffraction angle of 8.415°±0.2°, 11.512°±0.2°, 14.824°±0.2°, 17.087°±0.2°, 17.278°±0.2°, 19.461°±0.2°, 21.350°±0.2°, 22.344°±0.2° or 27.621°±0.2°;

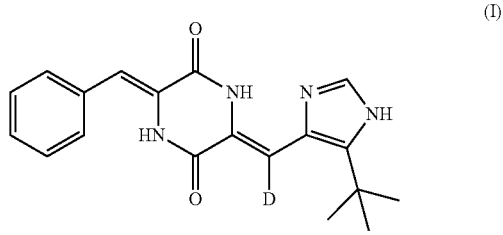 [SMILES: [2H]/C(c1nc[nH]c1C(C)(C)C)=c1/[nH]c(=O)/c(=C/c2ccccc2)[nH]c1=O]

(I)

preferably, said crystalline form has an X-ray powder diffraction characteristic peaks at 2θ diffraction angle of 8.415°±0.2°, 11.512°±0.2°, 14.824°±0.2°, 17.2780°±0.2°, 19.461°±0.2°, 21.3500°±0.2°, 22.344±0.2° and 27.621°±0.2°;

more preferably, said crystalline form has an X-ray powder diffraction characteristic peaks at 2θ diffraction angle of 8.415° 10.2°, 11.5120°±0.2°, 14.824°±0.2°, 17.087°±0.2°, 17.2780°±0.2°, 19.461°±0.2°, 21.350°±0.2°, 22.344°±0.2° and 27.621°±0.2°;

more preferably, said crystalline form has an X-ray powder diffraction characteristic peaks at 2θ diffraction angle of 8.415°±0.2°, 11.512°±0.2°, 12.271°±0.2°, 13.126°±0.2°, 13.618°±0.2°, 14.824°±0.2°, 16.011°±0.2°, 16.282°±0.2°, 17.087°±0.2°, 17.278°±0.2°, 17.608°±0.2°, 18.1340°±0.2°, 18.408°±0.2°, 19.461°±0.2°, 19.735°±0.2°, 20.745°±0.2°, 21.350°±0.2°, 22.344°±0.2°, 23.198°±0.2°, 24.874°±0.2°, 25.168°±0.2°, 26.997°±0.2°, 27.621°±0.2° and 28.479°±0.2°;

most preferably, the X-ray powder diffraction pattern of said crystalline form is consistent with FIG. 1.

Said crystalline form is named as α-crystalline form, the method for its preparation comprises the following steps:

cyclizing ethyl isocyanoacetate with trimethylacetic anhydride under alkaline condition to give 5-(tert-butyl) oxazole-4-ethyl formate;

converting 5-(tert-butyl)oxazole-4-ethyl formate to an imidazole ring under heating in formamide, followed by reduction by lithium aluminum hydride, oxidization by manganese dioxide, reduction by deuterated sodium borohydride, and deoxidization by manganese dioxide to give 5-(tert-butyl)-1H-imidazol-4-deuteroformaldehyde; dissolving glycine anhydride in acetic anhydride to give 1,4-diacetylpiperazine-2,5-dione;

condensing 5-(tert-butyl)-1H-imidazol-4-deuteroformaldehyde with 1,4-diacetylpiperazine-2,5-dione under alkaline condition, followed by condensation with benzaldehyde and purification to give an α-crystalline form of (3Z,6Z)-3-benzylidene-6-[(5-tert-butyl-1H-imidazol-4-yl)deuteromethylene]piperazine-2,5-dione as a pale-yellow crystalline powder.

In another aspect, the present invention also provides a crystalline form of (3Z,6Z)-3-benzylidene-6-[(5-tert-butyl-1H-imidazol-4-yl)deuteromethylene]piperazine-2,5-dione, and said crystalline form has at least three X-ray powder diffraction characteristic peaks at 2θ diffraction angle of 7.629°±0.2°, 8.052°±0.2°, 12.967°±0.2°, 15.327°±0.2°, 16.195°±0.2°, 23.194°±0.2°, 23.760°±0.2°, 24.129°±0.2°, 24.419°±0.2°, 26.465°±0.2° or 29.213°±0.2°;

preferably, said crystalline form has an X-ray powder diffraction characteristic peaks at 2θ diffraction angle of 7.629°±0.2°, 8.052°±0.2°, 12.967°±0.2°, 15.3270°±0.2°, 16.195°±0.2°, 23.194°±0.2°, 23.760°±0.2°, 24.129°±0.2°, 24.419°±0.2°, 26.465°±0.2° and 29.213°±0.2°;

more preferably, said crystalline form has an X-ray powder diffraction characteristic peaks at 2θ diffraction angle of 7.629°±0.2°, 8.052°±0.2°, 8.958°±0.2°, 12.967°±0.2°, 15.327°±0.2°, 16.1950°±0.2°, 16.606°±0.2°, 17.410°±0.2°, 23.194°±0.2°, 23.760°±0.2°, 24.1290°±0.2°, 24.419°±0.2°, 25.256°±0.2°, 26.465°±0.2° and 29.213°±0.2°;

most preferably, the X-ray powder diffraction pattern of said crystalline form is consistent with FIG. 2.

Said crystalline form is named as β-crystalline form, and its preparation method comprises the following steps: dissolving (3Z,6Z)-3-benzylidene-6-[(5-tert-butyl-1H-imidazol-4-yl)deuteromethylene]piperazine-2,5-dione completely till saturation using a solvent at 15° C. to 100° C., standing and cooling to 20° C.-30° C. in the absence of light, and naturally volatilizing the solvent to give a β-crystalline form of (3Z,6Z)-3-benzylidene-6-[(5-tert-butyl-1H-imidazol-4-yl)deuteromethylene]piperazine-2,5-dione, and said solvent is methanol, ethanol, isopropanol, acetone or water, or a mixed solvent of two or more thereof;

preferably, said solvent is a mixed solvent of water and methanol with a volume ratio of $V_{water}:V_{methanol}$ ranging from 1:1000 to 3:100, and the heating temperature for dissolution ranges from 60° C. to 80° C.

Further, said prepared β-crystalline form is a single crystal in which one molecule of (3Z,6Z)-3-benzylidene-6-[(5-tert-butyl-1H-imidazol-4-yl)deuteromethylene]piperazine-2,5-dione is combined with one molecule of methanol, and its appearance is cubic. It is analyzed by X-ray single crystal diffraction to be a monoclinic single crystal having a space group of P2(1)/n, its analytical structure is consistent with FIG. 3, and its melting point is 263.6° C. to 264.4° C.

In still another aspect, the present invention also provides a crystalline form of (3Z,6Z)-3-benzylidene-6-[(5-tert-butyl-1H-imidazol-4-yl)deuteromethylene]piperazine-2,5-dione, and said crystalline form has at least three X-ray powder diffraction characteristic peaks at 2θ diffraction angle of 8.075°±0.2°, 12.986°±0.2°, 16.217°±0.2°, 19.709°±0.2° or 24.441°±0.2°;

preferably, said crystalline form has an X-ray powder diffraction characteristic peaks at 2θ diffraction angle of 8.075°±0.2°, 12.986°±0.2°, 16.217°±0.2°, 19.709°±0.2° and 24.441°±0.2°;

more preferably, the X-ray powder diffraction pattern of said crystalline form is consistent with FIG. 4.

Said crystalline form is named as γ-crystalline form, and its preparation method comprises the following steps: dissolving (3Z,6Z)-3-benzylidene-6-[(5-tert-butyl-1H-imidazol-4-yl)deuteromethylene]piperazine-2,5-dione completely till saturation at 15° C. to 100° C. using methanol, ethanol, isopropanol, acetone or water or a mixed solvent of at least two thereof, standing and cooling to 15° C.-20° C. in the absence of light, and naturally volatilizing the solvent to give a γ-crystalline form of (3Z,6Z)-3-benzylidene-6-[(5-tert-butyl-1H-imidazol-4-yl)deuteromethylene]piperazine-2,5-dione.

Further, said solvent is a mixture of water and methanol with a volume ratio of $V_{water}:V_{methanol}$ ranging from 3:100 to 1:5, and the heating temperature for dissolution is 25° C. to 50° C.

Further, said prepared γ-crystalline form is a single crystal in which one molecule of (3Z,6Z)-3-benzylidene-6-[(5-tert-butyl-1H-imidazol-4-yl)deuteromethylene]piperazine-2,5-dione is combined with two molecules of methanol, and its appearance is diamond-shaped. It is analyzed by X-ray single crystal diffraction to be a triclinic single crystal having a space group of P-1, its analytical structure is consistent with FIG. 5, and its melting point is 263.6° C.-265.1° C.

In still another aspect, the present invention also provides a crystalline form of (3Z,6Z)-3-benzylidene-6-[(5-tert-butyl-1H-imidazol-4-yl)deuteromethylene]piperazine-2,5-dione monohydrate, and said crystalline form has at least three X-ray powder diffraction characteristic peaks at 2θ diffraction angle of 8.075°±0.2°, 12.988°+0.2°, 16.201°±0.2°, 17.545°±0.2° 19.084°±0.2°, 19.7240°±0.2°, 23.710°+0.2°, 24.422°±0.2°, 26.485°±0.2° or 29.234°±0.2°;

more preferably, said crystalline form has an X-ray powder diffraction characteristic peaks at 2θ diffraction angle of 8.075°±0.2°, 12.988°±0.2°, 16.201°±0.2°, 19.084°±0.2°, 19.724°±0.2°, 24.422°±0.2° and 29.234°±0.2°;

more preferably, said crystalline form has an X-ray powder diffraction characteristic peaks at 2θ diffraction angle of 8.075°±0.2°, 12.988°±0.2°, 16.201°±0.2°, 17.545°±0.2°, 19.084°±0.2°, 19.724°±0.2°, 23.710°±0.2°, 24.422°±0.2°, 26.485°±0.2° and 29.234°±0.2°;

more preferably, said crystalline form has an X-ray powder diffraction characteristic peaks at 2θ diffraction angle of 8.075°±0.2°, 9.145°±0.2°, 12.988°±0.2°, 14.740°±0.2°, 16.201°±±0.2°, 17.545°±0.2°, 18.367°±0.2°, 19.084°±0.2°, 19.724°±0.2°, 22.781°±0.2°, 23.710°±0.2°, 24.422°±0.2°, 25.279°±0.2°, 26.485°±0.2°, 27.867°±0.2° and 29.234°±0.2°;

most preferably, the X-ray powder diffraction pattern of said crystalline form is consistent with FIG. 6.

Said crystalline form is named as δ-crystalline from, and its preparation method comprises the following steps: recrystallizing (3Z,6Z)-3-benzylidene-6-[(5-tert-butyl-1H-imidazol-4-yl)deuteromethylene]piperazine-2,5-dione in a mixed solvent of water and an organic solvent, wherein said organic solvent is selected from at least one of an alkane saturated alcohol, an unsaturated alcohol, an alkane saturated amine and an unsaturated amine, cooling and stirring to precipitate to give a δ-crystalline form of (3Z,6Z)-3-benzylidene-6-[(5-tert-butyl-1H-imidazol-4-yl)deuteromethylene]piperazine-2,5-dione, and said crystalline form is a monohydrate of (3Z,6Z)-3-benzylidene-6-[(5-tert-butyl-1H-imidazol-4-yl)deuteromethylene]piperazine-2,5-dione, and its melting point is 263.5° C. to 266.5° C.

Further, said organic solvent is preferably methanol, ethanol, isopropanol or acetone; said mixed solvent comprises water and isopropanol with a volume ratio of $V_{water}:V_{isopropanol}$ ranging from 1:100 to 10:1, said mixed solvent comprises water and methanol with a volume ratio of $V_{water}:V_{methanol}$ ranging from 1:100 to 10:1, and said mixed solvent comprises water and ethanol with a volume ratio of $V_{water}:V_{ethanol}$ ranging from 1:100 to 10:1.

Further, placing the crude product of (3Z,6Z)-3-benzylidene-6-[(5-tert-butyl-1H-imidazol-4-yl)deuteromethylene]piperazine-2,5-dione in a reaction vessel, in the absence of light, adding isopropanol as solvent, heating to dissolve completely, then adding water with a volume ratio of $V_{water}:V_{isopropanol}$ ranging from 1:100 to 1:1, standing at −10° C. to 30° C., stirring and cooling to precipitate, followed by suction filtering, washing and drying to give a pale-yellow solid which is (3Z,6Z)-3-benzylidene-6-[(5-tert-butyl-1H-imidazol-4-yl)deuteromethylene]piperazine-2,5-dione monohydrate with high purity having a trans-isomer content of less than 0.1%, i.e. δ-crystalline form.

Further, said volume ratio of isopropanol to water is $V_{isopropanol}:V_{water}=5:2$, and the precipitation temperature preferably is −5° C. to 10° C.

Method of preparing a δ-crystalline single crystal of (3Z,6Z)-3-benzylidene-6-[(5-tert-butyl-1H-imidazol-4-yl)deuteromethylene]piperazine-2,5-dione comprises the following steps: dissolving (3Z,6Z)-3-benzylidene-6-[(5-tert-butyl-1H-imidazol-4-yl)deuteromethylene]piperazine-2,5-dione completely till saturation at 25° C. to 100° C. in methanol, ethanol, isopropanol, acetone or water or a mixed solvent of at least two thereof, in the absence of light, standing and cooling to 10° C. to 50° C., then naturally volatilizing the solvent to give a δ-crystalline single crystal of (3Z,6Z)-3-benzylidene-6-[(5-tert-butyl-1H-imidazol-4-yl)deuteromethylene]piperazine-2,5-dione.

Further, said prepared δ-crystalline form is a single crystal in which one molecule of (3Z,6Z)-3-benzylidene-6-[(5-tert-butyl-1H-imidazol-4-yl)deuteromethylene]piperazine-2,5-dione is combined with one molecule of water, and its appearance is needle-like. It is analyzed by X-ray single crystal diffraction to be a monoclinic single crystal having a space group of P2(1)/n, its analytical structure is consistent with FIG. 7, and its melting point is 263° C. to 267° C.

In still another aspect, the present invention also provides a crystalline form of (3Z,6Z)-3-benzylidene-6-[(5-tert-butyl-1H-imidazol-4-yl)deuteromethylene]piperazine-2,5-dione monoisopropylate, named as ε-crystalline form, and its preparation method comprises the following steps: dissolving (3Z,6Z)-3-benzylidene-6-[(5-tert-butyl-1H-imidazol-4-yl)deuteromethylene]piperazine-2,5-dione completely till saturation at 10° C. to 100° C. in a mixed solvent of isopropanol and water, in the absence of light, standing and cooling to 10° C. to 50° C., then naturally volatilizing the solvent to give a ε-crystalline form of (3Z,6Z)-3-benzylidene-6-[(5-tert-butyl-1H-imidazol-4-yl)deuteromethylene]piperazine-2,5-dione.

Further, the used solvent comprises purified water and isopropanol with a volume ratio of $V_{water}:V_{isopropanol}$ ranging from 1:200 to 1:10.

Further, said prepared ε-crystalline form is a single crystal in which one molecule of (3Z,6Z)-3-benzylidene-6-[(5-tert-butyl-1H-imidazol-4-yl)deuteromethylene]piperazine-2,5-dione is combined with one molecule of isopropanol, and its appearance is diamond-shaped. It is analyzed by X-ray single crystal diffraction to be a monoclinic single crystal having a space group of P2(1)/n, its analytical structure is consistent with so FIG. 9, and its melting point is 264.1° C. to 264.7° C.

In still another aspect, the present invention also provides a use of the aforementioned crystalline forms of (3Z,6Z)-3-benzylidene-6-[(5-tert-butyl-1H-imidazol-4-yl)deuteromethylene]piperazine-2,5-dione for preparation of antitumor drugs.

In still another aspect, the present invention also provides a crystalline form of (3Z,6Z)-3-benzylidene-6-[(5-tert-butyl-1H-imidazol-4-yl)methylene]piperazine-2,5-dione as shown in Formula (II), and said crystalline form has at least three X-ray powder diffraction characteristic peaks at 2θ diffraction angle of 7.670°±0.2°, 9.069°±0.2°, 15.383°±0.2°, 16.6680°±0.2°, 17.468°±0.2°, 18.109°±0.2°, 19.960°±0.20, 23.307°±0.2°, 23.836°±0.2°, 24.462°±0.2°, 28.046°±0.2° or 28.827°±0.2°;

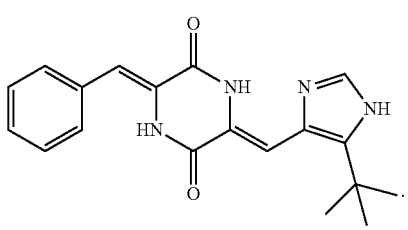

(II)

Preferably, said crystalline form has an X-ray powder diffraction characteristic peaks at 2θ diffraction angle of 7.670°±0.2°, 9.069°±0.2°, 15.383°±0.2°, 16.668°±0.2° and 23.836°±0.2°;

more preferably, said crystalline form has an X-ray powder diffraction characteristic peaks at 2θ diffraction angle of 7.670°±0.2°, 9.069°±0.2°, 15.383°±0.2°, 16.668°±0.2°, 17.4680°±0.2°, 18.109°±0.2°, 19.9600°±0.2°, 23.307°±0.2°, 23.836°±0.2°, 24.462°±0.2°, 28.046°±0.2° and 28.827°±0.2°;

more preferably, said crystalline form has an X-ray powder diffraction characteristic peaks at 2θ diffraction angle of 7.356°±0.2°, 7.670°±0.2°, 8.097°±0.2°, 9.069°±0.2°, 12.032°±0.2°, 12.500°±0.2°, 13.063°±0.2°, 15.3830°±0.2°, 16.241°±0.2°, 16.668°±0.2°, 17.468°±0.2°, 18.109°±0.2°, 18.694°±0.2°, 19.960°±0.2°, 23.307°±0.2°, 23.836°±0.2°, 24.462°±0.2°, 28.046°±0.2°, 28.827°±0.2° and 30.226°±0.2°;

most preferably, the X-ray powder diffraction pattern of said crystalline form is consistent with FIG. 11.

Said crystalline form is named as b-crystalline form, and its preparation method comprises the following steps: dissolving (3Z,6Z)-3-benzylidene-6-[(5-tert-butyl-1H-imidazol-4-yl)methylene]piperazine-2,5-dione completely till saturation at 40° C. to 100° C. in a mixed solvent of water and methanol with a volume ratio of $V_{water}$:$V_{methanol}$ ranging from 1:1000 to 3:100, in the absence of light, standing and cooling to 15° C. to 30° C., then naturally volatilizing the solvent to give a b-crystalline form of (3Z,6Z)-3-benzylidene-6-[(5-tert-butyl-1H-imidazol-4-yl)methylene]piperazine-2,5-dion e.

Further, said mixed solvent comprises water and methanol with a volume ratio of $V_{water}$:$V_{methanol}$ ranging from 1:1000 to 1:100, and the temperature for complete dissolution is 60° C. to 80° C.

Further, the prepared b-crystalline form is a single crystal in which one molecule of (3Z,6Z)-3-benzylidene-6-[(5-tert-butyl-1H-imidazol-4-yl)methylene]piperazine-2,5-dione is combined with one molecule of methanol, and its appearance is cubic. It is analyzed by X-ray single crystal diffraction to be monoclinic having a space group of P2(1)/n, its analytical structure is consistent with FIG. 12, and its melting point is 264.0° C. to 264.9° C.

In still another aspect, the present invention also provides a crystalline form of (3Z,6Z)-3-benzylidene-6-[(5-tert-butyl-1H-imidazol-4-yl)methylene]piperazine-2,5-dione, and said crystalline form has at least three X-ray powder diffraction characteristic peaks at 2θ diffraction angle of 7.918°±0.2°, 9.168°±0.2°, 12.014°±0.2°, 12.985°±0.2°, 18.382°±0.2° 18.616°±0.2°, 23.367°±0.2°, 25.203° 10.2° or 27.771°±0.2°;

preferably, said crystalline form has an X-ray powder diffraction characteristic peaks at 2θ diffraction angle of 7.918°±0.2°, 9.168°±0.2°, 18.382°±0.2° and 18.616°±0.2°;

more preferably, said crystal form has an X-ray powder diffraction characteristic peaks at 2θ diffraction angle of 7.918°±0.2°, 9.168°±0.2°, 12.014°±0.2°, 12.985°±0.2°, 18.382°±0.2°, 18.616°±0.2°, 23.367°±0.2°, 25.203°±0.2° and 27.771°±0.2°;

more preferably, said crystalline form has an X-ray powder diffraction characteristic peaks at 2θ diffraction angle of 7.918°±0.2°, 9.168°±0.2°, 9.905°±0.2°, 12.014°±0.2°, 12.985°±0.2°, 14.970°±0.2°, 15.873°±0.2°, 18.382°±0.2°, 18.616°±0.2°, 19.081°±0.2°, 19.881°±0.2°, 22.862°±0.2°, 23.367°±0.2°, 23.719°±0.2°, 24.073°±0.2°, 25.203°±0.2°, 26.447°±0.2°, 27.771°±0.2 and 37.787°±0.2°.

most preferably, the X-ray powder diffraction pattern of said crystalline form is consistent with FIG. 13.

Said crystalline form is named as c-crystalline form, and its preparation method comprises the following steps: dissolving (3Z,6Z)-3-benzylidene-6-[(5-tert-butyl-1H-imidazol-4-yl)methylene]piperazine-2,5-dione completely at 60° C. to 100° C. in a mixed solvent of water and methanol with a volume ratio of $V_{water}$:$V_{methanol}$ ranging from 3:100 to 1:5, in the absence of light, standing and cooling to 15° C. to 30° C., then naturally volatilizing the solvent to obtain a c-crystalline form of (3Z,6Z)-3-benzylidene-6-[(5-tert-butyl-1H-imidazol-4-yl)methylene]piperazine-2,5-dione.

Further, the volume ratio of water to methanol $V_{water}$:$V_{methanol}$ in said mixed solvent ranges from 3:100 to 1:20.

Further, the prepared c-crystalline form is a single crystal in which one molecule of (3Z,6Z)-3-benzylidene-6-[(5-tert-butyl-1H-imidazol-4-yl)methylene]piperazine-2,5-dione is combined with one molecule of methanol, and its appearance is needle-like. It is analyzed by X-ray single crystal diffraction to be monoclinic with a space group of P2(1)/n, its analytical structure is consistent with FIG. 14, and its melting point is 263.2° C. to 264.0° C.

In still another aspect, the present invention also provides a crystalline form of (3Z,6Z)-3-benzylidene-6-[(5-tert-butyl-1H-imidazol-4-yl)methylene]piperazine-2,5-dione, and said crystalline is a (3Z,6Z)-3-benzylidene-6-[(5-tert-butyl-1H-imidazol-4-yl)methylene]piperazine-2,5-dione monohydrate; preferably said crystalline form has at least three X-ray powder diffraction characteristic peaks at 2θ diffraction angle of 8.073°±0.2°, 13.005°±0.2°, 17.544°±0.2°, 18.382°±0.2°. 19.082°±0.2°, 19.707°±0.2°, 22.766°±0.2°, 23.759°±0.2°, 24.438°±0.2°, 25.277°±0.2°, 26.486°±0.2° or 29.234°±0.2°;

preferably, said crystalline form has an X-ray powder diffraction characteristic peaks at 2θ diffraction angle of 8.073°±0.2°, 13.005°±0.2°, 19.082°±0.2°, 19.707°±0.2° and 23.759°±0.2°;

more preferably, said crystalline form has an X-ray powder diffraction characteristic peaks at 2θ diffraction angle of 8.073°±0.2, 13.005°±0.2°, 17.544°±0.2°, 18.382°±0.2°, 19.082°±0.2°, 19.707°±0.2°, 22.766°±0.2°, 23.759°±0.2°, 24.438°±0.2°, 25.277°±0.2°, 26.486°±0.2° and 29.234°±0.2°;

more preferably, said crystalline form has an X-ray powder diffraction characteristic peaks at 2θ diffraction angle of 8.073°±0.2°, 9.146°±0.2°, 13.005°±0.2°, 14.740°±0.2°, 16.184±0.2°, 17.544°±0.2°, 18.382°±0.2°, 19.082°±0.2°, 19.707°±0.2°, 22.766°±0.2°, 23.759°±0.2°, 24.438°±0.2°, 25.277°±0.2°, 26.486°±0.2°, 27.883°±0.2° and 29.234°±0.2°;

most preferably, the X-ray powder diffraction pattern of said crystalline form is to consistent with FIG. 15.

Said crystalline form is named as d-crystalline form, and its preparation method comprises the following steps: recrystallizing (3Z,6Z)-3-benzylidene-6-[(5-tert-butyl-1H-imidazol-4-yl)methylene]piperazine-2,5-dione in a mixed solvent of water and an organic solvent, wherein said organic solvent is selected from at least one of an alkane saturated alcohol, an unsaturated alcohol, an alkane saturated amine or an unsaturated amine, cooling and stirring to precipitate to give a d-crystalline form of (3Z,6Z)-3-benzylidene-6-[(5-tert-butyl-1H-imidazol-4-yl)methylene]piperazine-2,5-dione, and said crystalline form is a monohydrate, and its melting point is 263.5° C. to 266.5° C.

Further, the volume ratio of water to isopropanol $V_{water}$:$V_{isopropanol}$ in said mixed solvent ranges from 1:100 to 99:100.

Further, the volume ratio of water to isopropanol $V_{water}$:$V_{isopropanol}$ in said mixed solvent ranges from 1:10 to 9:10.

Further, placing the crude product of (3Z,6Z)-3-benzylidene-6-[(5-tert-butyl-1H-imidazol-4-yl)methylene]piperazine-2,5-dione in a reaction vessel, in the absence of light, adding isopropanol as solvent, dissolving completely under heating, then adding water with a volume ratio of $V_{isopropanol}$:$V_{water}$ ranging from 1:10 to 100:1, standing at −15° C. to 30° C., stirring and cooling to precipitate, followed by suction filtering, washing and drying to give a pale-yellow solid which is a monohydrate of (3Z,6Z)-3-benzylidene-6-[(5-tert-butyl-1H-imidazol-4-yl)methylene]piperazine-2,5-dione with high purity having a trans-isomer content of less than 0.1%.

Further, said volume ratio of isopropanol to water is $V_{isopropanol}$:$V_{water}$=5:2.

The present invention provides a method of preparing a d-crystalline single crystal of (3Z,6Z)-3-benzylidene-6-[(5-tert-butyl-1H-imidazol-4-yl)methylene]piperazine-2,5-dione, comprising the following steps: dissolving (3Z,6Z)-3-benzylidene-6-[(5-tert-butyl-1H-imidazol-4-yl)methylene]piperazine-2,5-dione completely till saturation at 25° C. to 100° C. in methanol, ethanol, isopropanol, acetone or water or a mixed solvent of at least two thereof, in the absence of light, standing and cooling to 10° C. to 50° C., then naturally volatilizing the solvent to give a d-crystalline form of (3Z,6Z)-3-benzylidene-6-[(5-tert-butyl-1H-imidazol-4-yl)methylene]piperazine-2,5-dione.

Further, the used solvent comprises water and isopropanol with a volume ratio of $V_{water}$:$V_{isopropanol}$ ranging from 1:200 to 7:20.

Further, the used solvent comprises water and ethanol with a volume ratio of $V_{water}$:$V_{isopropanol}$ ranging from 1:200 to 1:2.

Said d-crystalline form prepared according to aforementioned method is a single crystal in which one molecule of (3Z,6Z)-3-benzylidene-6-[(5-tert-butyl-1H-imidazol-4-yl) methylene]piperazine-2,5-dione is combined with one molecule of water, and its appearance is long columnar or needle-like. It is analyzed by X-ray single crystal diffraction to be a monoclinic single crystal with a space group of P2(1)/n, its analytical structure is consistent with FIG. 17, and its melting point is 263° C. to 267° C.

In still another aspect, the present invention also provides a method of preparing and purifying a dehydrophenylahistin-like compound with high purity, and said method comprises the following steps: placing the crude product of a dehydrophenylahistin-like compound in a reaction vessel, in the absence of light, adding isopropanol or methanol or ethanol or n-butanol under heating condition till complete dissolution of said compound, then adding water resulting in no crystalline precipitation, standing at 15° C. to 30° C., stirring and cooling to precipitate, followed by suction filtering, washing and drying to give a dehydrophenylahistin-like compound with high-purity.

Further, said dehydrophenylahistin-like compound has a structure represented by Formula (III):

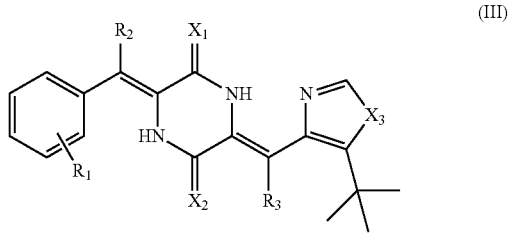

(III)

wherein $R_1$ is a mono-substituted to penta-substituted substituent group on the benzene ring, which is independently selected from hydrogen, deuterium, 3-benzoylphenyl, 3-(4-methoxybenzoyl)phenyl, 3-(4-fluorobenzoyl)phenyl, halogen, hydroxy, methoxy, amino, phenyl, aminomethylphenyl, C1-C24 alkyl, C2-C24 alkenyl, C2-C24 alkynyl, arylalkyl, heterocycloarylalkyl, C1-C24 acyl, C1-C24 alkoxy, carboxy, carboxylate, acylamino, N-monosubstituted or N,N-disubstituted acylamino, sulfo, sulphonate, sulphonylamino, N-substituted sulphonylamino, alkoxy, arylalkoxy, alkylsulfanyl, cyano, amino, substituted amino, nitro, cycloalkyl, cycloalkenyl, aryl, substituted aryl, heterocycloaryl, aryloxy, aroyl, epoxy group, cycloacyl, arylsulfenyl, arylsulfonyl;

$R_2$ is hydrogen or deuterium, and $R_3$ is hydrogen or deuterium;

$X_1$ is oxygen or sulfur, and $X_2$ is oxygen or sulfur;

$X_3$ is —NH, oxygen or sulfur;

further, when said dehydrophenylahistin-like compound is (3Z,6Z)-3-benzylidene-6-[(5-tert-butyl-1H-imidazol-4-yl)deuteromethylene]piperazine-2,5-dione, in particular, when preparing a (3Z,6Z)-3-benzylidene-6-[(5-tert-butyl-1H-imidazol-4-yl)deuteromethylene]piperazine-2,5-dione monohydrate with high purity, the crude product of (3Z,6Z)-3-benzylidene-6-[(5-tert-butyl-1H-imidazol-4-yl)deuteromethylene]piperazine-2,5-dione is placed in a reaction vessel, in the absence of light, isopropanol is added as solvent, completely dissolving under heating, water is added then with the resulting volume ratio of $V_{isopropanol}$:$V_{water}$ ranging from 1:5 to 100:1, standing at −10° C. to 30° C., stirring and cooling to precipitate, suction filtered, washed and dried to give a pale-yellow solid which is a monohydrate of (3Z, 6Z)-3-benzylidene-6-[(5-tert-butyl-1H-imidazol-4-yl)deuteromethylene]piperazine-2,5-dione with high purity having a trans-isomer content of less than 0.1%.

Further, said volume ratio of isopropanol to water is $V_{isopropanol}:V_{water}=5:2$.

Alternatively, said dehydrophenylahistin-like compound is (3Z,6Z)-3-benzylidene-6-[(5-tert-butyl-1H-imidazol-4-yl)methylene]piperazine-2,5-dione, and method of preparing the crude product of (3Z,6Z)-3-benzylidene-6-[(5-tert-butyl-1H-imidazol-4-yl)methylene]piperazine-2,5-dione compound is as follows:

cyclizing ethyl isocyanoacetate with trimethylacetic anhydride under alkaline condition to give 5-(tert-butyl) oxazole-4-ethyl formate;

then converting 5-(tert-butyl)oxazole-4-ethyl formate into an imidazole ring under heating in formamide, followed by reduction by lithium aluminum hydride, and oxidization by manganese dioxide to give 5-(tert-butyl)-1H-imidazole-4-formaldehyde; dissolving glycine anhydride in acetic anhydride to give 1,4-diacetylpiperazine-2,5-dione;

condensing 5-(tert-butyl)-1H-imidazole-4-formaldehyde with 1,4-diacetylpiperazine-2,5-dione under alkaline condition, then further condensing with benzaldehyde to give a crude product of (3Z,6Z)-3-benzylidene-6-[(5-tert-butyl-1H-imidazol-4-yl)methylene]piperazine-2,5-dione.

Further, placing the crude product of (3Z,6Z)-3-benzylidene-6-[(5-tert-butyl-1H-imidazol-4-yl)methylene]piperazine-2,5-dione in a reaction vessel, in the absence of light, adding isopropanol as solvent and dissolving completely under heating, adding water with a volume ratio of $V_{isopropanol}:V_{water}$ ranging from 1:10 to 100:1, standing at −15° C. to 30° C., stirring and cooling to precipitate, followed by suction filtering, washing and drying to give a pale-yellow solid which is a (3Z,6Z)-3-benzylidene-6-[(5-tert-butyl-1H-imidazol-4-yl)methylene]piperazine-2,5-dione monohydrate with high purity having a trans-isomer content of less than 0.1%.

Further, said volume ratio of isopropanol to water is $V_{isopropanol}:V_{water}=5:2$.

Further, said 5-(tert-butyl)-1H-imidazole-4-ethyl formate is purified by the following steps: reacting 5-(tert-butyl)-1H-oxazole-4-ethyl formate with formamide under heating, after the reaction is completed, cooling the solution, extracting with sodium carbonate and petroleum ether, separating the impurities in petroleum ether phase, extracting with ethyl acetate, combining the organic phases, washing with water, drying and concentrating under reduced pressure to give a concentrated solution which, while being warm, is poured into water, stirred and pulpified till a solid precipitates, followed by suction filtering, washing and drying in vacuo to give a purified 5-(tert-butyl)-1H-imidazole-4-ethyl formate as mentioned above.

Further, said 1,4-diacetylpiperazine-2,5-dione is purified by the following steps: refluxing and reacting of glycine anhydride with acetic anhydride, after the reaction is completed, cooling the resulting solution to room temperature, concentrating under reduced pressure to evaporate the solvent, dissolving the concentrate in dichloromethane, filtering through diatomite, concentrating under reduced pressure to remove dichloromethane, recrystallizing in ethyl acetate, precipitating at low temperature, filtering and drying to give a purified 1,4-diacetylpiperazine-2,5-dione.

The advantages and technical effects of the present invention are: in view of drug polymorphism, dominant drug crystalline form is extremely important for the stability of drug quality. No polymorphs of (3Z,6Z)-3-benzylidene-6-[(5-tert-butyl-1H-imidazol-4-yl)deuteromethylene]piperazine-2,5-dione has been reported so far. A thorough study on polymorphs of said compound has been conducted in the present invention, and the inventors found that the δ-crystalline form of (3Z,6Z)-3-benzylidene-6-[(5-tert-butyl-1H-imidazol-4-yl)deuteromethylene]piperazine-2,5-dione is a monohydrate, which is very stable in stress testing when exposed to high temperature, high humidity and illumination, and in accelerated stability testing, while the α-crystalline form of said compound is easily transformed into the δ-crystalline form under high humidity condition, and the β, γ and ε-crystalline forms are not stable enough under high temperature condition which results in the loss of crystallization solvent, and partial crystalline forms may also be transformed into the δ-crystalline form under high humidity condition. Meanwhile, all β, γ and ε-crystalline forms of (3Z,6Z)-3-benzylidene-6-[(5-tert-butyl-1H-imidazol-4-yl) deuteromethylene]piperazine-2,5-dione contain crystallization solvent, which exceeds the requirement on residual solvent content in an API and therefore are not suitable for drug development. Based on the aforementioned consideration and experimental verification, said δ-crystalline form has excellent stability and safety.

Plinabulin has been in Phase III clinical study, and as its formulation is an injection, the stability of API is particularly important. The present invention studies the polymorphs of plinabulin, and in light of drug stability of said polymorphs, the present invention determines that the d-crystalline form of (3Z,6Z)-3-benzylidene-6-[(5-tert-butyl-1H-imidazol-4-yl)methylene]piperazine-2,5-dione is a monohydrate, wherein said crystalline form is easily prepared with high stability. While a-crystalline form has certain hygroscopicity and is easily transformed into a d-crystalline form under high humidity condition, b- and c-crystalline forms contain organic solvent which results in high residual solvent and therefore are not suitable for drug development. The d-crystalline form as a monohydrate is not easy to lose its water molecule, and has excellent molecular stability during preparation and storage processes. Its quality and pharmaceutical efficacy during drug development are not altered. Therefore, the d-crystalline form is the most beneficial form of the compound disclosed herein.

The benzylidene group in the structure of both (3Z,6Z)-3-benzylidene-6-[(5-tert-butyl-1H-imidazol-4-yl)deuteromethylene]piperazine-2,5-dione and (3Z,6Z)-3-benzylidene-6-[(5-tert-butyl-1H-imidazol-4-yl)methylene]piperazine-2,5-dione is a double bond, which is highly prone to cis-trans isomerization under illumination condition to produce isomer impurities, posing certain safety risk for drug development. The present invention provides methods of preparing and purifying monohydrates of both (3Z,6Z)-3-benzylidene-6-[(5-tert-butyl-1H-imidazol-4-yl)deuteromethylene]piperazine-2,5-dione and (3Z,6Z)-3-benzylidene-6-[(5-tert-butyl-1H-imidazol-4-yl)methylene]piperazine-2,5-dione with high purities, with the merits of being easy to operate, high yield and high purity. Isomer impurities in the product can be controlled to be less than 0.1%, and the aforementioned monohydrates as solid APIs can remain stable under high temperature, high humidity and illumination conditions in stress testing, without isomerization or change in the content of impurities.

DETAILED DESCRIPTION OF EMBODIMENTS

Figure 1:
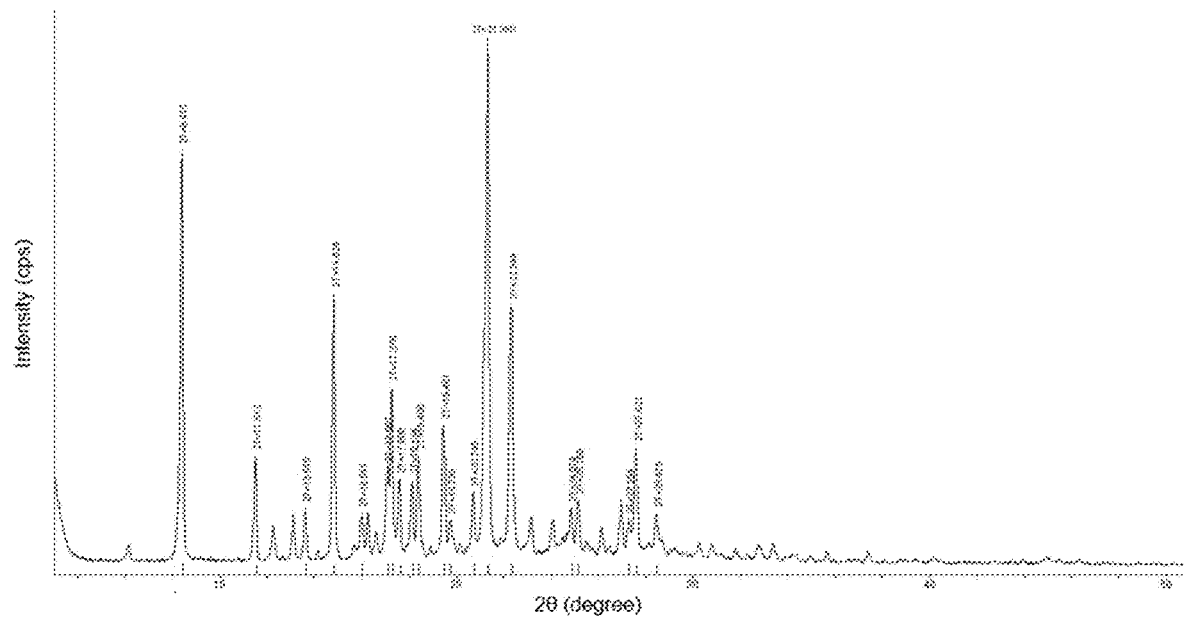
FIG. 1 shows an X-ray powder diffraction pattern of the α-crystalline form of (3Z,6Z)-3-benzylidene-6-[(5-tert-butyl-1H-imidazol-4-yl)deuteromethylene]piperazine-2,5-dione of the present invention.

The technical solutions of the present invention are further described in detail below with reference to the accompanying drawings and specific embodiments.

Example 1

Preparation of (3Z,6Z)-3-benzylidene-6-[(5-tert-butyl-1H-imidazol-4-yl)deuteromethylene]piperazine-2,5-dione The specific preparation process comprises the following steps:

1) Preparation of 5-(tert-butyl)oxazole-4-ethyl formate 90 g (796 mmol) of ethyl isocyanoacetate was added to 1000 mL of tetrahydrofuran, followed by slow dropwise addition of 145 g (955 mmol) of DBU and dropwise addition of 178 g (955 mmol) of trimethylacetic anhydride. The obtained was stirred at room temperature for 48 hours, after the reaction is completed, the reaction solution was concentrated under reduced pressure. The concentrate was extracted, 1500 mL of dichloromethane was added, followed by successive washing with 800 mL of 10% sodium carbonate, 800 mL of 10% citric acid, 800 mL of saturated brine. The aqueous phase was back-extracted twice with 1000 mL of dichloromethane. The organic phases were combined, dried over anhydrous sodium sulfate for half an hour, suction filtered, concentrated under reduced pressure, and filtered through a silica gel (200-300 mesh) column (EA:PE=1:10, 1:8, 1:5) to give 177 g of said 5-(tert-butyl)oxazole-4-ethyl formate as a yellow liquid.

2) Preparation of 5-(tert-butyl)-1H-imidazole-4-ethyl formate 157 g (796 mmol) of 5-(tert-butyl)-1H-oxazole-4-ethyl formate was added to 717 g (15.914 mol) of formamide, let stand in an oil bath at 180° C., stirred under reflux for 30 hours, cooled to room temperature, extracted and added with 800 mL of 10% sodium carbonate. 500 mL of petroleum ether was added to extract and the organic phase was discarded. Then extracted three times with ethyl acetate (1000 mL*3). The organic phases were combined and washed twice with saturated brine (800 mL*2). The aqueous phase was back-extracted twice with ethyl acetate (500 mL*2). The organic phases were combined and dried over anhydrous sodium sulfate, suction filtered, concentrated under reduced pressure, pulpified, stirred after addition of 1000 mL of water and then suction filtered. The filter cake was washed with water and dried in vacuo at 50° C. to give 71 g of 5-(tert-butyl)-1H-imidazole-4-ethyl formate as a earthy solid with a yield of 45%.

3) Preparation of 5-(tert-butyl)-1H-imidazole-4-methanol 40 g (1054 mmol) of lithium aluminum hydride was added to 300 mL of dried tetrahydrofuran in a cold trap at −10° C., 70 g (357 mmol) of 5-(tert-butyl)-1H-imidazole-4-ethyl formate in 200 mL of tetrahydrofuran was slowly added dropwise to the turbid lithium aluminum hydride solution. The mixture was moved to room temperature and stirred for 3 hours before quenched by ice-water, the reaction mixture was added dropwise to an appropriate amount of ice in a measuring cup. The resulting mixture was suction filtered, and the filter cake was successively washed twice with water (1000 mL*2), twice with tetrahydrofuran (500 mL*2), twice with anhydrous ethanol (500 mL*2), followed by concentration under reduced pressure, dehydration once by 95% ethanol and twice by anhydrous ethanol to give 51 g of said 5-(tert-butyl)-1H-imidazole-4-methanol as a pale-yellow solid with a yield of 93%.

4) Preparation of 5-(tert-butyl)-1H-imidazole-4-formaldehyde 50 g (324 mmol) of 5-(tert-butyl)-1H-imidazole-4-methanol was added to 500 mL of dichloromethane, followed by addition of 282 g (3242 mmol) of manganese dioxide. The reaction was stirred at room temperature for 24 hours. The mixture was suction filtered and added with diatomite. The filter cake was washed three times with anhydrous ethanol (500 mL*3) and concentrated under reduced pressure to give 43 g of said 5-(tert-butyl)-1H-imidazole-4-formaldehyde as a pale-yellow solid with a yield of 87%.

5) Preparation of 5-(tert-butyl)-1H-imidazole-4-deuteromethanol 17 g (112 mmol) of 5-(tert-butyl)-1H-imidazole-4-formaldehyde was dissolved in 110 mL of ethanol at −10° C., followed by batchwise addition of 14 g (336 mmol) of sodium borodeuteride. The reaction was carried out for 20 hours, quenched by 200 mL of saturated ammonium chloride and concentrated under reduced pressure. The resulting concentrate was extracted with 500 mL of saturated potassium carbonate and ethyl acetate. The organic phases were combined, dried, concentrated with reduced pressure and pulpified with a 50:1 mixture of petroleum ether and ethyl acetate to give 13 g of said 5-(tert-butyl)-1H-imidazole-4-deuteromethanol as a white solid with a yield of 74%.

6) Preparation of 5-(tert-butyl)-1H-imidazole-4-deuteroformaldehyde 12.90 g (82.57 mmol) of 5-(tert-butyl)-1H-imidazole-4-deuteromethanol was added to 150 mL of dichloromethane, followed by addition of 71.79 g (825.74 mmol) of manganese dioxide. The reaction was stirred at 30° C. for 40 hours. The mixture was filtered by suction, washed with 1000 mL of ethyl acetate and concentrated under reduced pressure to give 10.00 g of said 5-(tert-butyl)-1H-imidazole-4-deuteroformaldehyde with a yield of 79%.

7) Preparation of N,N-diacetylpiperazine-2,5-dione 50 g (438 mmol) of glycine anhydride was added into 179 g (1753 mmol) of acetic anhydride. The mixture was placed in an oil bath at 155° C. and stirred under reflux for 30 hours, concentrated under reduced pressure, dissolved in dichloromethane and filtered through diatomite and silica gel. The resulting filter cake was rinsed with dichloromethane, concentrated under reduced pressure and recrystallized in ethyl acetate at 70° C. to give 74 g of said N,N-diacetylpiperazine-2,5-dione as a brown solid with a yield of 85%.

8) Preparation of (Z)-1-acetyl-3-[(5-(tert-butyl)-1H-imidazol-4-yl)deuteromethylene]piperazine-2,5-dione 10.00 g (65.27 mmol) of 5-(tert-butyl)-1H-imidazol-4-deuteroformaldehyde was added to 50 mL of DMF, followed by addition of 25.88 g (130.59 mmol) of N,N-diacetylpiperazine-2,5-dione. The resulting solution was repeatedly exhausted under nitrogen protection for three times. 31.91 g (97.94 mmol) of cesium carbonate was added and the mixture was repeatedly exhausted under nitrogen protection for three times. The reaction was stirred at room temperature for 20 hours in the absence of light, the reaction solution was then poured into ice-water (400 mL) and filtered by suction. The resulting filter cake was successively washed with water (200 mL*2) and an 8:1 mixture of petroleum ether and ethyl acetate (200 mL), then ultrasonically dispersed in ethanol and dichloromethane. The insolubles was filtered off and the resulting filtrate was concentrated under reduced pressure, dehydrated by anhydrous ethanol and pulpified with ethyl acetate (250 mL) to give 8.96 g of said (Z)-1-acetyl-3-[(5-(tert-butyl)-1H-imidazol-4-yl)deuteromethylene]piperazine-2,5-dione as a brown-yellow solid with a yield of 47.11%.

9) Preparation of (3Z,6Z)-3-benzylidene-6-[(5-tert-butyl-1H-imidazol-4-yl)deuteromethylene]piperazine-2,5-dione 8.84 g (30.33 mmol) of (Z)-1-acetyl-3-[(5-(tert-butyl)-1H-imidazol-4-yl) deuteromethylene]piperazine-2,5-dione was added to 25 mL of DMF, followed by addition of 4.83 g (45.51 mmol) of benzaldehyde. The resulting solution was repeatedly exhausted under nitrogen protection for three times. 14.82 g (45.49 mmol) of cesium carbonate was added and the mixture was repeatedly exhausted under nitrogen protection for three times. The temperature was programmed to reach 50° C. and the reaction was stirred for 24 hours. The reaction solution was poured into ice-water (300 mL) and filtered by suction. The resulting filter cake was successively washed with 200 mL*2 water and an 8:1 mixture of petroleum ether and ethyl acetate (200 mL), then ultrasonically dispersed in ethanol (50 mL) and ethyl acetate (160 mL). The insolubles was filtered off and the resulting filtrate was concentrated under reduced pressure, dehydrated by anhydrous ethanol, ultrasonically dispersed in 150 mL of ethyl acetate, let stand at −18° C. overnight and filtered by suction. The resulting filter cake was washed with icy ethyl acetate (50 mL) to give 6.66 g of said (3Z,6Z)-3-benzylidene-6-[(5-tert-butyl-1H-imidazole-4-yl)deuteromethylene]piperazine-2,5-dione as a yellow-green solid with a yield of 65.09%. $^1$H NMR (500 MHz, dmso) δ12.30 (s, 1H), δ12.22 (s, 1H), 10.00 (brs, 1H), 7.82 (d, J=12.7 Hz, 1H), 7.51 (d, J=7.6 Hz, 2H), 7.40 (t, J=7.7 Hz, 2H), 7.30 (t, J=7.4 Hz, 1H), 6.73 (s, 1H), 1.37 (s, 9H).

Example 2

Purification Process of (3Z,6Z)-3-benzylidene-6-[(5-tert-butyl-1H-imidazol-4-yl)deuteromethylene] piperazine-2,5-dione and preparation of its α-crystalline form 6.66 g of above obtained crude product of (3Z,6Z)-3-benzylidene-6-[(5-tert-butyl-1H-imidazol-4-yl)deuteromethylene]piperazine-2,5-dione was placed in a brown bottle, 400 mL of isopropanol was added under heating till said crude product was completely dissolved. 160 mL of water was added resulting in no crystalline precipitation. The resulting solution was stirred and cooled to precipitate at room temperature and filtered by suction. The resulting filter cake was washed with a 1:1 mixture of isopropanol and water, pulpified with 100 mL of ethyl acetate for 10 hours and filtered. The resulting filter cake was washed with ethyl acetate and dried to give 5.323 g of a yellow powder solid with a yield of 80.0%. The crystalline form of the obtained solid was α-crystalline form and its main X-ray powder diffraction characteristic peaks at 2θ diffraction angle are shown in Table 1, and the specific diffraction pattern is shown in FIG. 1.

Table 1 shows data on powder XRD analysis of the α, β, γ, δ-crystalline forms of (3Z,6Z)-3-benzylidene-6-[(5-tert-butyl-1H-imidazol-4-yl)deuteromethylene]piperazine-2,5-dione of the present invention.

TABLE 1

Powder XRD characteristic peaks of the
α-, β-, γ-, δ-crystalline forms

| Content tested | α-crystalline from | β-crystalline form | γ-crystalline form | δ-crystalline from |
|---|---|---|---|---|
| Main XRD powder diffraction characteristic absorption peaks | 8.415° | 7.629° | 8.075° | 8.075° |
| | 11.512° | 8.052° | 12.986° | 9.145° |
| | 12.271° | 8.958° | 16.217° | 12.988° |
| | 13.126° | 12.967° | 19.709° | 14.740° |
| | 13.618° | 15.327° | 24.441° | 16.201° |
| | 14.824° | 16.195° | | 17.545° |
| | 16.011° | 16.606° | | 18.367° |
| | 16.282° | 17.410° | | 19.084° |
| | 17.087° | 23.194° | | 19.724° |
| | 17.278° | 23.760° | | 22.781° |
| | 17.608° | 24.129° | | 23.710° |
| | 18.134° | 24.419° | | 24.422° |
| | 18.408° | 25.256° | | 25.279° |
| | 19.461° | 26.465° | | 26.485° |
| | 19.735° | 29.213° | | 27.867° |
| | 20.745° | | | 29.234° |
| | 21.350° | | | |
| | 22.344° | | | |
| | 23.198° | | | |
| | 24.874° | | | |
| | 25.168° | | | |
| | 26.997° | | | |
| | 27.621° | | | |
| | 28.479° | | | |

Example 3

Figure 2:
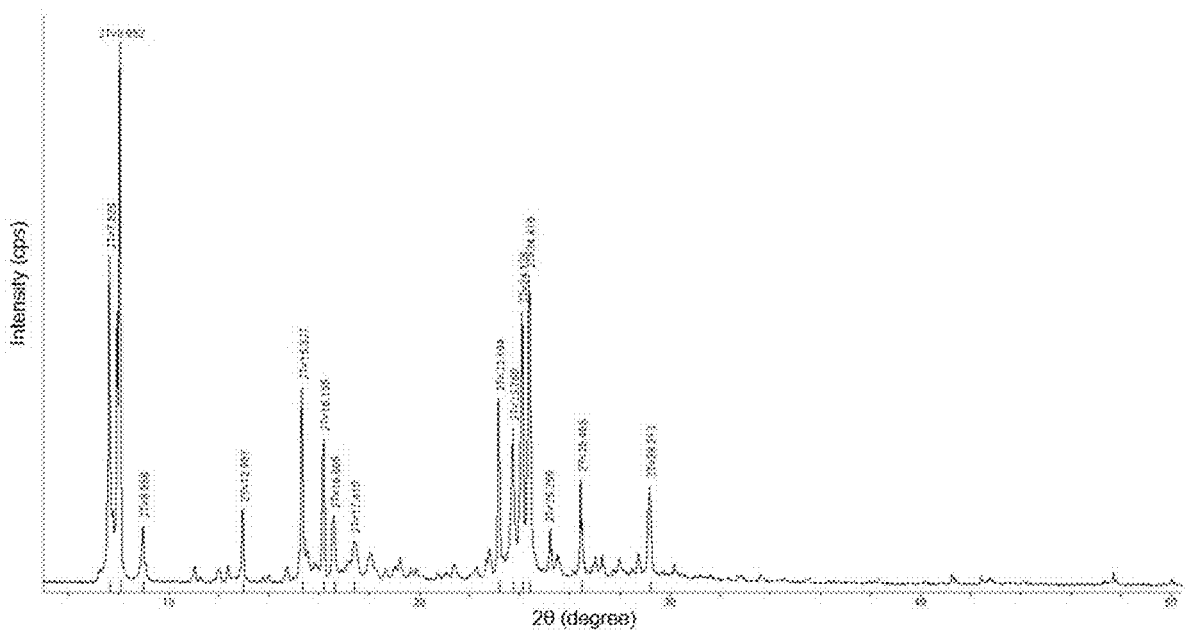
FIG. 2 shows an X-ray powder diffraction pattern of the β-crystalline form of (3Z,6Z)-3-benzylidene-6-[(5-tert-butyl-1H-imidazol-4-yl)deuteromethylene]piperazine-2,5-dione of the present invention.

Preparation of a β-Crystalline Form of (3Z,6Z)-3-benzylidene-6-[(5-tert-butyl-1H-imidazol-4-yl)deuteromethylene]piperazine-2,5-dione The specific preparation process comprises the following steps: weighing and dissolving (3Z,6Z)-3-benzylidene-6-[(5-tert-butyl-1H-imidazol-4-yl)deuteromethylene]piperazine-2,5-dione (200 mg, 0.59 mmol) in a mixed solution of 20 mL of methanol and 0.1 mL of water at 70° C., filtering into a crystallizing dish with its opening covered with a piece of plastic wrap membrane in which holes were made by a capillary having an outer diameter of 0.5 mm, letting stand to volatilize in the absence of light at 25° C. to precipitate a β-crystalline form of crystal 72 hours later, filtering and drying to give 142 mg of a cubic solid with a yield of 71%. The melting point of the obtained β-crystalline form is 263.6° C. to 264.4° C. The obtained β-crystalline form was examined by X-ray powder diffraction test, and its characteristic peaks at 2θ diffraction angle are shown in Table 1. The specific X-ray powder diffraction pattern is shown in FIG. 2.

Figure 3:
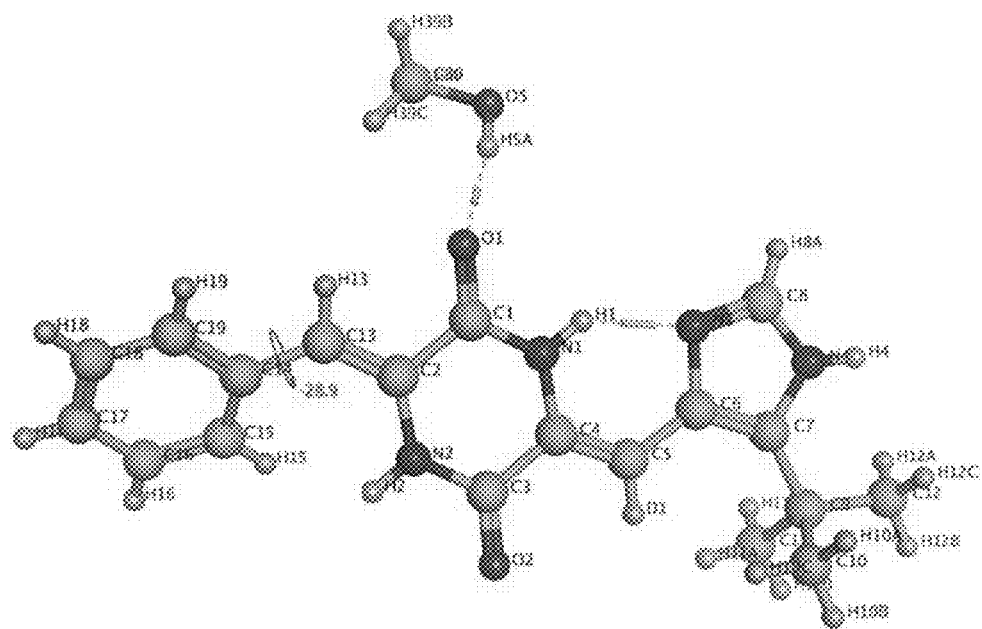
FIG. 3 shows an analytical structure diagram of X-ray single crystal diffraction of the β-crystalline form of (3Z,6Z)-3-benzylidene-6-[(5-tert-butyl-1H-imidazol-4-yl)deuteromethylene]piperazine-2,5-dione of the present invention.

The β-crystalline form prepared above is determined as a single crystal in which one molecule of (3Z,6Z)-3-benzylidene-6-[(5-tert-butyl-1H-imidazol-4-yl)deuteromethylene]piperazine-2,5-dione is combined with one molecule of methanol. X-ray single crystal diffraction test is carried out on a Bruker X-ray single crystal diffractometer using Cu-Kα radiation (λ=1.54178 Å) at the temperature of 293.2K, with compound size set to be 0.45 mm×0.43 mm×0.36 mm and data collected at θ angle of 4.05 to 66.40 degrees. The test results of crystallographic parameters are shown in Table 2 below, and the analytical structure is shown in FIG. 3.

TABLE 2

Crystallographic parameters

| Parameter | Test results | | |
|---|---|---|---|
| Emprical formula | $C_{20}H_{23}DN_4O_3$ | | |
| Molecular weight | 369.44 | | |
| Crystal system | monoclinic | | |
| Space group | P2(1)/n | | |
| Unit cell dimentions | a = 14.6192(7) Å | α = 90 deg. | |
| | b = 17.0390(8) Å | β = 103.564(2) deg. | |
| | c = 16.0709(11) Å | γ = 90 deg. | |
| Volume | 3891.5(4) Å$^3$ | | |
| Z, calculated density | 8, 1.261 Mg/m$^3$ | | |
| Absorption coefficient | 0.703 mm$^{-1}$ | | |
| Number of electrons in a unit cell | 1568 | | |
| Crystallite size | 0.45 × 0.43 × 0.36 mm | | |
| Limiting indices | −161 ≤ h ≤ 17, −20 ≤ k ≤ 20, −18 ≤ l ≤ 19 | | |
| Collected/unique diffraction data | 13581/6839 [R(int) = 0.0411] | | |
| Completeness to θ = 66.40 | 100.0% | | |
| Absorption correction parameters | Semi-empirical from equivalents | | |
| Max. and min transmission | 0.7860 and 0.7428 | | |
| Refinement method | Full-matrix least-squares on F$^2$ | | |
| Data/restraints/parameters | 6839/0/496 | | |
| Goodness-of-fit on F$^2$ | 1.056 | | |
| Final R indices | R1 = 0.0576, wR2 = 0.1534 | | |
| R indices (all data) | R1 = 0.0904, wR2 = 0.1765 | | |
| Light absorption coefficient | 0.00105(12) | | |
| Largest diff. peak and valley | 0.223 and 0.188 e · Å$^{-3}$ | | |

Example 4

Figure 4:
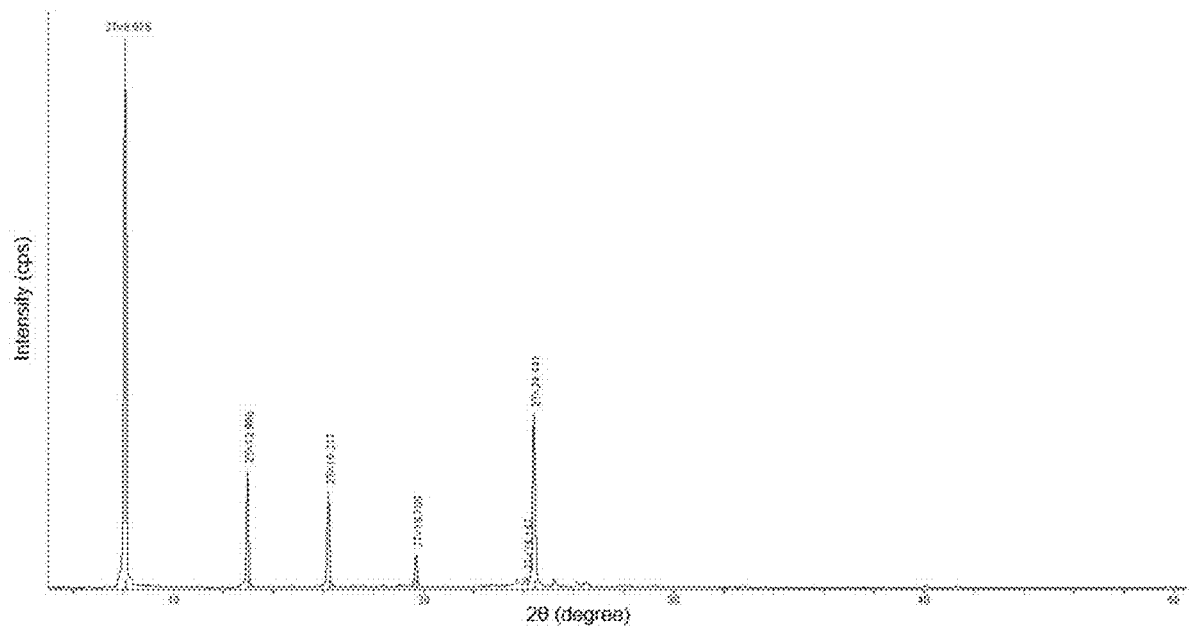
FIG. 4 shows an X-ray powder diffraction pattern of the γ-crystalline form of (3Z,6Z)-3-benzylidene-6-[(5-tert-butyl-1H-imidazol-4-yl)deuteromethylene]piperazine-2,5-dione of the present invention.

Preparation of a γ-Crystalline Form of (3Z,6Z)-3-benzylidene-6-[(5-tert-butyl-1H-imidazol-4-yl)deuteromethylene]piperazine-2,5-dione The specific preparation process comprises the following steps: weighing and dissolving (3Z,6Z)-3-benzylidene-6-[(5-tert-butyl-1H-imidazol-4-yl)deuteromethylene]piperazine-2,5-dione (100 mg, 0.30 mmol) in a mixed solvent of 13 mL of methanol and 0.52 mL of water at 30° C., filtering into a crystallizing dish and inoculating with seed crystals, covering the opening of crystallizing dish with a piece of plastic wrap membrane in which holes were made by a capillary with an outer diameter of 0.5 mm, letting stand to volatilize at 18° C. in the absence of light to precipitate a γ-crystalline form of crystal 72 hours later, filtering and drying to give 38 mg of a diamond-shape solid with a yield of 38%. The melting point of the obtained γ-crystalline form is 263.6° C. to 265.1° C. The obtained γ-crystalline form was analyzed by X-ray powder diffraction test, and its characteristic peaks at 2θ diffraction angle are shown in Table 1. The specific X-ray powder diffraction pattern is shown in FIG. 4.

19

Figure 5:
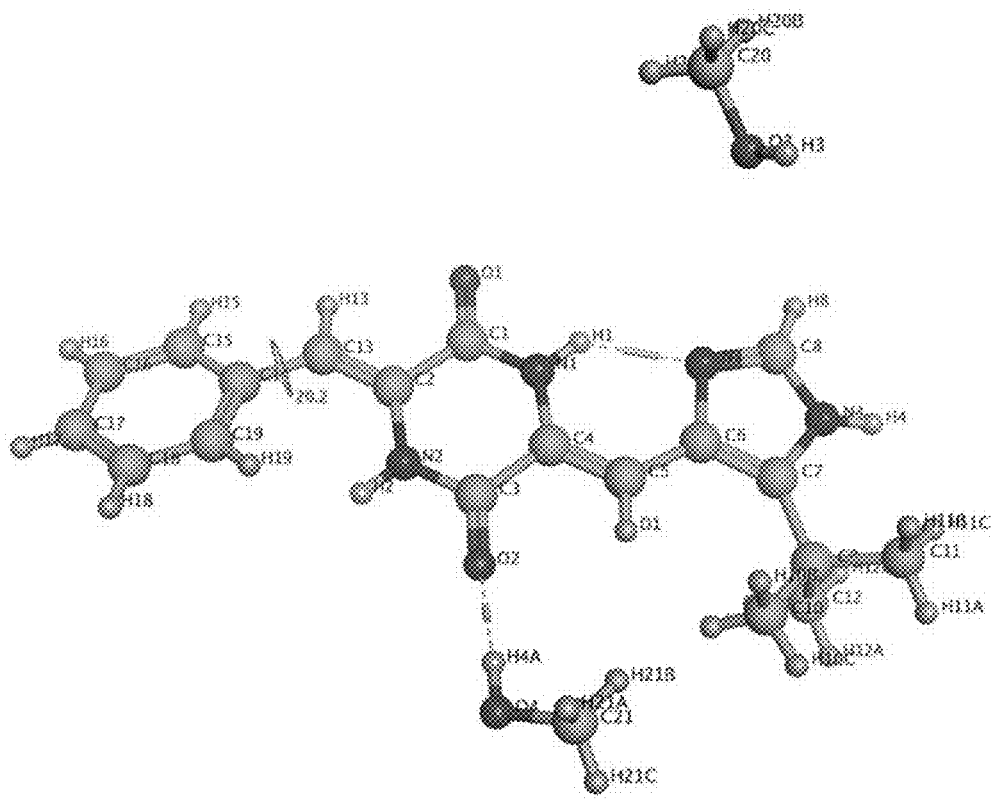
FIG. 5 shows an analytical structure diagram of X-ray single crystal diffraction of the γ-crystalline form of (3Z,6Z)-3-benzylidene-6-[(5-tert-butyl-1H-imidazol-4-yl)deuteromethylene]piperazine-2,5-dione of the present invention.

The γ-crystalline form is determined as a single crystal in which one molecule of (3Z,6Z)-3-benzylidene-6-[(5-tertbutyl-1H-imidazol-4-yl)deuteromethylene]piperidine-2, 5-dione is combined with two molecules of methanol. X-ray single crystal diffraction test is carried out on a Bruker X-ray single crystal diffractometer equipped with Cu-Kα radiation (λ=1.54178 Å) at the temperature of 293K, with compound size set to be 0.50 mm×0.40 mm×0.18 mm and data collected at θ angle of 3.79 to 66.38 degrees. The test results of crystallographic parameters are shown in Table 3 below, and the analytical structure is shown in FIG. 5.

TABLE 3

Crystallographic parameters

| Parameter | Test results | |
|---|---|---|
| Emprical formula | $C_{21}H_{27}DN_4O_4$ | |
| Molecular weight | 401.48 | |
| Crystal system | triclinic | |
| Space group | P-1 | |
| Unit cell dimensions | a = 9.4485(9) Å | α = 101.769(2) deg. |
| | b = 10.1149(10) Å | β = 96.7290(10) deg. |
| | c = 12.1258(13) Å | γ = 105.604(2) deg. |
| Volume | 1074.35(19) Å$^3$ | |
| Z, calculated density | 2, 1.241 Mg/m$^3$ | |
| Absorption coefficient | 0.701 mm$^{-1}$ | |
| Number of electrons in a unit cell | 428 | |
| Crystallite size | 0.50 × 0.40 × 0.18 mm | |
| Limiting indices | −11 ≤ h ≤ 11, −7 ≤ k ≤ 12, −14 ≤ l ≤ 14 | |
| Collected/unique diffraction data | 6293/3765 [R(int) = 0.0289] | |
| Completeness to θ = 66.40 | 99.9% | |
| Absorption correction parameters | Semi-empirical from equivalents | |
| Max. and min transmission | 0.8828 and 0.7179 | |
| Refinement method | Full-matrix least-squares on F$^2$ | |
| Data/restraints/parameters | 3765/0/267 | |
| Goodness-of-fit on F$^2$ | 1.064 | |
| Final R indices | R1 = 0.0570, wR2 = 0.1555 | |
| R indices (all data) | R1 = 0.0815, wR2 = 0.1789 | |
| Light absorption coefficient | 0.0076(10) | |
| Largest diff. peak and valley | 0.492 and 0.239 e · Å$^{-3}$ | |

Example 5

Figure 6:
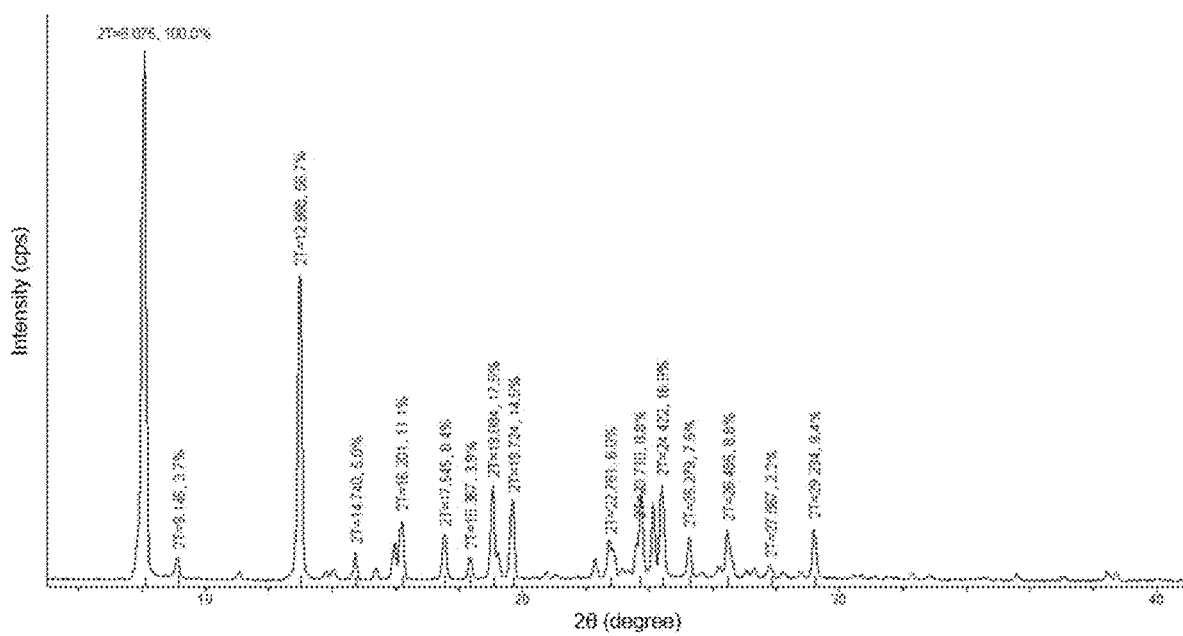
FIG. 6 shows an X-ray powder diffraction pattern of the δ-crystalline form of (3Z,6Z)-3-benzylidene-6-[(5-tert-butyl-1H-imidazol-4-yl)deuteromethylene]piperazine-2,5-dione of the present invention.

Preparation of a δ-Crystalline Form of (3Z,6Z)-3-benzylidene-6-[(5-tert-butyl-1H-imidazol-4-yl)deuteromethylene]piperazine-2,5-dione The specific preparation process comprises the following steps: weighing and dissolving said (3Z,6Z)-3-benzylidene-6-[(5-tert-butyl-1H-imidazol-4-yl)deuteromethylene]piperazine-2,5-dione solid (1.00 g, 2.96 mmol) in 60 mL of isopropanol at 80° C., filtering upon heating, letting the filtrate stand at 80° C., adding 12 ml of water dropwise, stirring the clear solution to precipitate at room temperature for 6 hours, filtering and drying to give 0.95 g of a yellow powder crystalline solid with a yield of 90.41%. The obtained δ-crystalline form was analyzed by X-ray powder diffraction test exhibiting characteristic absorption peaks at 2θ diffraction angle of 8.075°, 9.145°, 12.988°, 14.740°, 16.201°, 17.545°, 18.367°, 19.084°, 19.724°, 22.781°, 23.710°, 24.422°, 25.279°, 26.485°, 27.867°, 29.234°, the 2θ diffraction angle error is ±0.2°, see FIG. 6.

Figure 8:
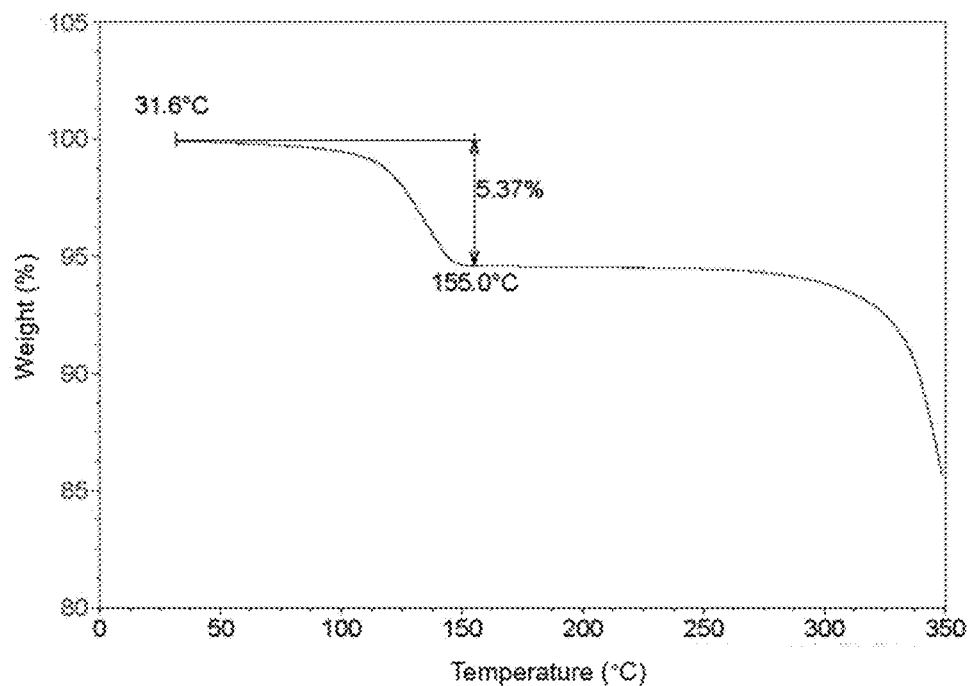
FIG. 8 shows a thermogravimetric analysis diagram of the δ-crystalline form of (3Z,6Z)-3-benzylidene-6-[(5-tert-butyl-1H-imidazol-4-yl)deuteromethylene]piperazine-2,5-dione of the present invention.

The obtained δ-crystalline form is a monohydrate of (3Z,6Z)-3-benzylidene-6-[(5-tert-butyl-1H-imidazol-4-yl)deuteromethylene]piperazine-2,5-dione, containing 5.314% water as determined by a Karl Fischer moisture meter. FIG. 8 shows the data support from a thermogravimetric analysis diagram, wherein the element analysis is shown in Table 4 below:

20

TABLE 4

Data on element analysis of the δ-crystalline form

| Sample | Determination value (%) | Theratical value (%) |
|---|---|---|
| δ-crystalline form of (3Z,6Z)-3-benzylidene-6[(5-tert-butyl-1H-imidazol-4-yl)deuteromethylene]-piperazine-2,5-dione | C: 64.19<br>N: 15.78<br>H: 6.24 | C: 64.21<br>N: 15.76<br>H: 6.27 |

Example 6

Preparation of a δ-Crystalline Single Crystal of (3Z,6Z)-3-benzylidene-6-[(5-tert-butyl-1H-imidazol-4-yl)deuteromethylene]piperazine-2,5-dione Method One The specific preparation process comprises the following steps: weighing and dissolving (3Z,6Z)-3-benzylidene-6-[(5-tert-butyl-1H-imidazol-4-yl)deuteromethylene]piperazine-2,5-dione (100 mg, 0.30 mmol) in a mixed solvent of 13 mL of methanol and 0.52 mL of water at 30° C., filtering into a crystallizing dish and inoculating with seed crystals, covering the opening of crystallizing dish with a piece of plastic wrap membrane in which holes were made using a capillary with an outer diameter of 0.5 mm, letting stand to volatilize at 13° C. in the absence of light to precipitate a δ-crystalline form of crystal 72 hours later, filtering and drying to give 34 mg of a needle-like solid with a yield of 34%. The melting point of the obtained δ-crystalline form is 264.4° C. to 266.2° C., and its characteristic absorption peaks at 2θ diffraction angle analyzed by X-ray powder diffraction test are consistent with those of FIG. 6.

Figure 7:
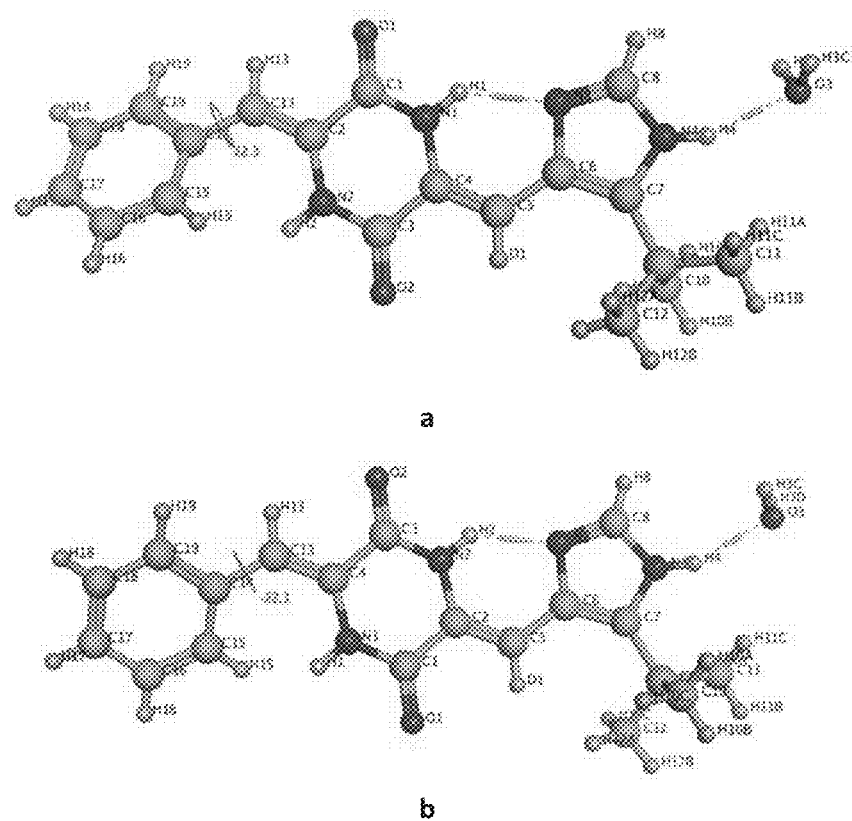
FIG. 7 shows an analytical structure diagram of X-ray single crystal diffraction of the δ-crystalline form of (3Z,6Z)-3-benzylidene-6-[(5-tert-butyl-1H-imidazol-4-yl)deuteromethylene]piperazine-2,5-dione of the present invention, wherein a is the crystalline analytical structure obtained by method one, and b is the crystalline analytical structure obtained by method two.

The δ-crystalline form prepared above is determined as a single crystal in which one molecule of (3Z,6Z)-3-benzylidene-6-[(5-tert-butyl-1H-imidazol-4-yl)deuteromethylene]piperazine-2,5-dione is combined with one molecule of water. X-ray single crystal diffraction test is carried out on a Bruker X-ray single crystal diffractometer equipped with Cu-Kα radiation (λ=1.54178 Å) at the temperature of 293K, with compound size set to be 0.42 mm×0.41 mm×0.40 mm and data collected at θ angle of 4.05 to 66.40 degrees. The test results of crystallographic parameters are shown in Table 5-1 below, and the analytical structure is shown as structure a in FIG. 7.

TABLE 5-1

Crystallographic parameters

| Parameter | Test results | |
|---|---|---|
| Emprical formula | $C_{19}H_{21}DN_4O_3$ | |
| Molecular weight | 355.41 | |
| Crystal system | monoclinic | |
| Space group | P2(1)/c | |
| Unit cell dimensions | a = 9.7051(5) Å | α = 90 deg. |
| | b = 8.5247(5) Å | β = 97.6520(10) deg. |
| | c = 22.0068(12) Å | γ = 90 deg. |
| Volume | 1804.48(17) Å$^3$ | |
| Z, calculated density | 4, 1.308 Mg/m$^3$ | |
| Absorption coefficient | 0.737 mm$^{-1}$ | |
| Number of electrons in a unit cell | 752 | |
| Crystallite size | 0.42 × 0.41 × 0.40 mm | |
| Limiting indices | −6 ≤ h ≤ 11, −9 ≤ k ≤ 10, −26 ≤ l ≤ 26 | |
| Collected/unique diffraction data | 6052/3171 [R(int) = 0.0326] | |
| Completeness to θ = 66.40 | 100.0% | |
| Absorption correction parameters | Semi-empirical from equivalents | |

TABLE 5-1-continued

| Crystallographic parameters | |
|---|---|
| Parameter | Test results |
| Max. and min transmission | 0.7569 and 0.7470 |
| Refinement method | Full-matrix least-squares on $F^2$ |
| Data/restraints/parameters | 3171/0/240 |
| Goodness-of-fit on $F^2$ | 1.055 |
| Final R indices | R1 = 0.0483, wR2 = 0.1269 |
| R indices (all data) | R = 0.0659, wR2 = 0.1408 |
| Light absorption coefficient | 0.0210(10) |
| Largest diff. peak and valley | 0.237 and 0.194 e · Å$^{-3}$ |

Method Two:

The specific preparation process comprises the following steps: weighing and dissolving (3Z,6Z)-3-benzylidene-6-[(5-tert-butyl-1H-imidazol-4-yl)deuteromethylene]piperazine-2,5-dione (100 mg, 0.30 mmol) in a mixed solvent of 15 mL of anhydrous ethanol and 1 mL of water at 65° C., filtering into a crystallizing dish with its opening covered with a piece of plastic wrap membrane in which holes were made by a capillary with an outer diameter of 0.5 mm, letting stand to volatilize at 26° C. in the absence of light to precipitate a δ-crystalline form of crystal 72 hours later, filtering and drying to give 51 mg of a long columnar solid with a yield of 49%. The melting point of the δ-crystalline form obtained is 264.9° C. to 266.1° C., and its characteristic absorption peaks at 20 diffraction angles analyzed by X-ray powder diffraction test are consistent with those of FIG. 6.

The δ-crystalline form prepared above is determined as a single crystal in which one molecule of (3Z,6Z)-3-benzylidene-6-[(5-tert-butyl-1H-imidazol-4-yl)deuteromethylene]piperazine-2,5-dione is combined with one molecule of water. X-ray single crystal diffraction test is carried out on a Bruker X-ray single crystal diffractometer using Cu-Kα radiation (λ=1.54178 Å) at the temperature of 293K, with compound size set to be 0.45 mm×0.43 mm×0.32 mm and data collected at θ angle of 4.05 to 66.20 degrees. The test results of crystallographic parameters are shown in Table 5-2 below, and the analytical structure is shown as structure b in FIG. 7.

TABLE 5-2

| Crystallographic parameters | |
|---|---|
| Parameter | Test results |
| Emprical formula | $C_{19}H_{21}DN_4O_3$ |
| Molecular weight | 355.41 |
| Crystal system | monoclinic |
| Space group | P2(1)/c |
| Unit cell dimensions | a = 9.7077(5) Å  α = 90 deg. |
| | b = 8.5222(5) Å  β = 97.652(2) deg. |
| | c = 22.0126(12) Å  γ = 90 deg. |
| Volume | 1804.91(17) Å$^3$ |
| Z, calculated density | 4, 1.308 Mg/m$^3$ |
| Absorption coefficient | 0.737 mm$^{-1}$ |
| Number of electrons in a unit cell | 752 |
| Crystallite size | 0.45 × 0.43 × 0.32 mm |
| Limiting indices | −11 ≤ h ≤ 11, −7 ≤ k ≤ 10, −24 ≤ l ≤ 26 |
| Collected/unique diffraction data | 5797/3149 [R(int) = 0.0335] |
| Completeness to θ = 66.20 | 100.0% |
| Absorption correction | Semi-empirical from equivalents |
| parameters | |
| Max. and min transmission | 0.7983 and 0.7326 |
| Refinement method | Full-matrix least-squares on $F^2$ |
| Data/restraints/parameters | 3149/0/240 |
| Goodness-of-fit on $F^2$ | 1.038 |
| Final R indices | R1 = 0.0492, wR2 = 0.1320 |
| R indices (all data) | R1 = 0.0620, wR2 = 0.1425 |

TABLE 5-2-continued

| Crystallographic parameters | |
|---|---|
| Parameter | Test results |
| Light absorption coefficient | 0.03060(15) |
| Largest diff. peak and valley | 0.225 and −0.186 e · Å$^{-3}$ |

Example 7

Hygroscopicity Test of the δ-Crystalline Form of (3Z,6Z)-3-benzylidene-6-[(5-tert-butyl-1H-imidazol-4-yl)deuteromethylene]piperazine-2,5-dione The test was conducted according to the general rule 9103 of guiding principle for drug hygroscopicity test in Chinese Pharmacopoeia 2015 edition Volume IV, and the results are shown in Table 6.

TABLE 6

| Hygroscopicity test results | | | | |
|---|---|---|---|---|
| Batch no. | Weight of weighing bottle (mg) | Weight of Sample + weighing bottle (mg) | Left for 24 h, Weight of Sample + weighing bottle (mg) | Weight gain (mg) | Hygro-scopicity |
| 20150401 | 30117.46 | 30423.60 | 30423.80 | 0.20 | none |
| 20150402 | 32498.44 | 32801.17 | 32801.41 | 0.24 | none |
| 20150403 | 29458.09 | 29765.76 | 29765.96 | 0.20 | none |

With bottle opened for 24 hours, weight gain percentage of the δ-crystalline form were less than 0.2%, indicating the δ-crystalline form is basically not hygroscopic according to the definition on hygroscopicity and hygroscopic weight gain in the Chinese Pharmacopoeia.

Studies on other crystalline forms of (3Z,6Z)-3-benzylidene-6-[(5-tert-butyl-1H-imidazol-4-yl)deuteromethylene]piperazine-2,5-dione indicate that the α-crystalline form has certain hygroscopicity and may partially transform into δ-crystalline form under 60% humidity condition. Meanwhile, the β and γ-crystalline forms have no hygroscopicity, but most of which may transform into δ-crystalline form after being stirred in water for 3 hours.

Example 8

Stress Testing and Accelerated Stress Testing of the δ-Crystalline Form of (3Z,6Z)-3-benzylidene-6-[(5-tert-butyl-1H-imidazol-4-yl)deuteromethylene]piperazine-2,5-dione In accordance with the general rule 9001 of guiding principles for stability tests of APIs and preparations in the Chinese Pharmacopoeia 2015 edition Volume IV, stress testing of the δ-crystalline form of (3Z,6Z)-3-benzylidene-6-[(5-tert-butyl-1H-imidazol-4-yl)deuteromethylene]piperazine-2,5-dione was conducted under high temperature, high humidity and illumination conditions, the sample batch number was 20150401, and the results are shown in Tables 7, 8 and 9 below.

TABLE 7

Data on high-temperature stress test of the δ-crystalline form

| Item tested | Limit requirement | High-temperature test/60° C. (days) | | |
|---|---|---|---|---|
| | | 0 | 5 | 10 |
| Appearance | Yellow crystalline powder | Yellow powder | Yellow powder | Yellow powder |
| Relevant substance (HPLC) | Impurity A ≤ 0.1% Impurity D ≤ 0.1% Other single impurity ≤ 0.1% Total impurities ≤ 0.5% | Impurity A: <LOQ (0.035%) Impurity D: 0.06% Other single impurity: not detected Total impurities: 0.07% | Impurity A: <LOQ (0.035%) Impurity D: 0.06% Other single impurity: not detected Total impurities: 0.07% | Impurity A: <LOQ (0.035%) Impurity D: 0.06% Other single impurity: not detected Total impurities: 0.07% |
| Content (HPLC) | 98.0%-102.0% (calculated as an anhydride) | 99.7% | 99.4% | 99.8% |

TABLE 8

Data on high-humidity stress test of the δ-crystalline form

| Item tested | Limit requirement | High-humidity test/25° C., 90% RH (days) | | |
|---|---|---|---|---|
| | | 0 | 5 | 10 |
| Appearance | Yellow crystalline powder | Yellow powder | Yellow powder | Yellow powder |
| Relevant substance (HPLC) | Impurity A ≤ 0.1% Impurity D ≤ 0.1% Other single impurity ≤ 0.1% Total impurities ≤ 0.5% | Impurity A: <LOQ (0.035%) Impurity D: 0.06% Other single impurity: not detected Total impurities: 0.07% | Impurity A: <LOQ (0.035%) Impurity D: 0.06% Other single impurity: not detected Total impurities: 0.07% | Impurity A: <LOQ (0.035%) Impurity D: 0.06% Other single impurity: not detected Total impurities: 0.07% |
| Content (HPLC) | 98.0%-102.0% (calculated as an anhydride) | 99.7% | 99.5% | 99.6% |

TABLE 9

Data on illumination stress test of the δ-crystalline form

| Item tested | Limit requirement | Illumination test/4500 Lx ± 500 Lx (days) | | |
|---|---|---|---|---|
| | | 0 | 5 | 10 |
| Appearance | Yellow crystalline powder | Yellow powder | Yellow powder | Yellow powder |
| Relevant substance (HPLC) | Impurity A ≤ 0.1% Impurity D ≤ 0.1% Other single impurity ≤ 0.1% Total impurities ≤ 0.5% | Impurity A: <LOQ (0.035%) Impurity D: 0.06% Other single impurity: not detected Total impurities 0.07% | Impurity A: <LOQ (0.035%) Impurity D: 0.05% Other single impurity: not detected Total impurities: 0.05% | Impurity A: <LOQ (0.035%) Impurity D: 0.05% Other single impurity: not detected Total impurities: 0.05% |
| Content (HPLC) | 98.0%-102.0% (calculated as an anhydride) | 99.7% | 100.1% | 99.8% |

Experiments show that the δ-crystalline form of (3Z,6Z)-3-benzylidene-6-[(5-tert-butyl-1H-imidazol-4-yl)deuteromethylene]piperazine-2,5-dione is relatively stable when let stand in high-temperature (60° C.), high-humidity (25° C., 90% RH) or illumination (4500 Lx±500 Lx) condition for 10 days. The α-crystalline form of (3Z,6Z)-3-benzylidene-6-[(5-tert-butyl-1H-imidazol-4-yl)deuteromethylene]piperazine-2,5-dione absorbs moisture easily to transform into δ-crystalline form under high-humidity condition, and the β-, γ- and ε-crystalline forms are not stable enough under high-temperature condition causing the loss of crystallization solvents, and some of these crystalline forms may transform into δ-crystalline form under high-humidity condition. As the β-, γ- and ε-crystalline forms of (3Z,6Z)-3-benzylidene-6-[(5-tert-butyl-1H-imidazol-4-yl)deuteromethylene]piperazine-2,5-dione contain crystallization solvent, exceeding the corresponding limit requirement in APIs, therefore these three crystalline forms are not suitable for further drug development. Based on the aforementioned consideration and experimental verification, the δ-crystalline form shows excellent stability and safety.

Meanwhile, a 6-month accelerated stability test was conducted on the δ-crystalline form of (3Z,6Z)-3-benzylidene-6-[(5-tert-butyl-1H-imidazol-4-yl)deuteromethylene]piperazine-2,5-dione. The sample batch number was 20150404. Factory packaging was simulated. The test conditions were 40° C.±2° C./75%±5% RH. The results are shown in Table 10 below.

TABLE 10

Data on accelerated stability test of the δ-crystalline form

| Item tested | Limit requirement | Observation period (months) | | | | |
|---|---|---|---|---|---|---|
| | | 0 | 1 | 2 | 3 | 6 |
| Apperance | Yellow crystalline powder | Yellow powder | Yellow powder | Yellow powder | Yellow powder | Yellow powder |
| Relevant substance (HPLC) | Impurity A ≤ 0.1% impurity D ≤ 0.1% Other single impurity ≤ 0.1% Total impurities ≤ 0.5% | < LOQ (0.035%) 0.06% Not detected 0.07% | < LOQ (0.035%) 0.06% Not detected 0.08% | < LOQ (0.035%) 0.06% Not detected 0.08% | < LOQ (0.035%) 0.06% Not detected 0.08% | < LOQ (0.035%) 0.06% Not detected 0.08% |
| Content (HPLC) | 98.0%-102.0% (Calculated as an anhydride) | 99.5% | 99.6% | 100.2% | 99.8% | 99.7% |

Results indicate that the δ-crystalline form of (3Z,6Z)-3-benzylidene-6-[(5-tert-butyl-1H-imidazol-4-yl)deuteromethylene]piperazine-2,5-dione shows excellent stability during the 6-month accelerated stress test, which provides a solid foundation for its pharmaceutical research.

Example 9

Preparation of an ε-Crystalline Form of (3Z,6Z)-3-benzylidene-6-[(5-tert-butyl-1H-imidazol-4-yl)deuteromethylene]piperazine-2,5-dione The specific preparation process comprises the following steps: weighing and dissolving (3Z,6Z)-3-benzylidene-6-[(5-tert-butyl-1H-imidazol-4-yl)deuteromethylene]piperazine-2,5-dione (100 mg, 0.30 mmol) in a mixed solvent of 15 mL of isopropanol and 0.30 mL of purified water at 55° C., filtering into a crystallizing dish with its opening covered with a piece of plastic wrap membrane in which holes were made using a capillary with an outer diameter of 0.5 mm, letting stand to volatilize at 15° C. in the absence of light to precipitate an ε-crystalline form 48 hours later, filtering and drying to give 45 mg of a diamond-shape solid with a yield of 45%. The melting point of obtained ε-crystalline form is 264.1° C. to 264.7° C.

Figure 9:
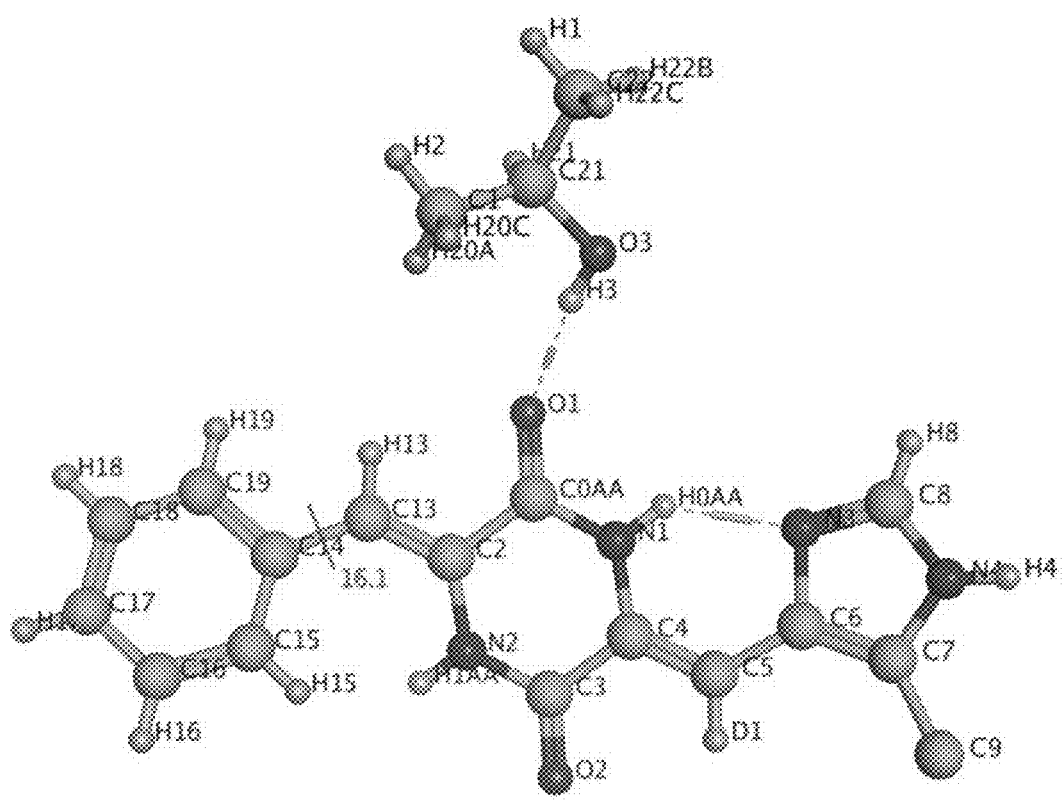
FIG. 9 shows an analytical structure diagram of X-ray single crystal diffraction of the ε-crystalline form of (3Z,6Z)-3-benzylidene-6-[(5-tert-butyl-1H-imidazol-4-yl)deuteromethylene]piperazine-2,5-dione of the present invention.

The ε-crystalline form is determined as a single crystal in which one molecule of (3Z,6Z)-3-benzylidene-6-[(5-tert-butyl-1H-imidazol-4-yl)deuteromethylene]piperazine-2,5-dione is combined with one molecule of isopropanol. X-ray single crystal diffraction test is carried out on a Bruker X-ray single crystal diffractometer using Cu-Kα radiation (λ=1.54178 Å) at the temperature of 293K, with compound size set to be 0.42 mm×0.28 mm×0.12 mm and data collected at θ angle of 3.82 to 66.05 degrees. The results of crystallographic parameters test are shown in Table 11 below, and the analytical structure is shown in FIG. 9.

TABLE 11

| Crystallographic parameters | |
|---|---|
| Parameter | Test results |
| Emprical formula | $C_{22}H_{27}DN_4O_3$ |
| Molecular weight | 397.49 |
| Crystal system | monoclinic |
| Space group | P2(1)/c |
| Unit cell dimensions | a = 11.7836(10)Å  α = 90 deg. |
| | b = 8.3648(9) Å  β = 101.181(9) deg. |
| | c = 22.778(2) Å  γ = 90 deg. |
| Volume | 2202.6(4) Å$^3$ |
| Z, calculated density | 4, 1.199 Mg/m$^3$ |
| Absorption coefficient | 0.654 mm$^{-1}$ |
| Number of electrons in a unit cell | 752 |
| Crystallite size | 0.42 × 0.28 × 0.12 mm |
| Limiting indices | -13 <= h <= 10, -9 <= k <= 9, -26 <= l <= 26 |
| Collected/unique diffraction data | 7493/3832 [R(int) = 0.0559] |
| Completeness to θ = 66.40 | 99.9% |
| Absorption correction parameters | Semi-empirical from equivalents |
| Max. and min transmission | 0.9257 and 0.7708 |
| Refinement method | Full-matrix least-squares on F$^2$ |
| Data/restraints/parameters | 3832/0/295 |
| Goodness-of-fit on F$^2$ | 1.081 |
| Final R indices | R1 = 0.0646, wR2 = 0.1372 |
| R indices (all data) | R1 = 0.1223, wR2 = 0.1700 |
| Light absorption coefficient | 0.0088(5) |
| Largest diff. peak and valley | 0.245 and -0.235 e · Å$^{-3}$ |

Example 10

Preparation of an α-Crystalline Form of (3Z,6Z)-3-benzylidene-6-[(5-tert-butyl-1H-imidazol-4-yl)methylene]piperazine-2,5-dione The specific preparation process includes the following steps:

1) Preparation of 5-(tert-butyl)oxazole-4-ethyl formate 90 g (796 mmol) of ethyl isocyanoacetate was added to 1000 mL of tetrahydrofuran, followed by slow dropwise addition of 145 g (955 mmol) of DBU and dropwise addition of 178 g (955 mmol) of trimethylacetic anhydride. The reaction was stirred at room temperature for 48 hours. After the reaction was complete, the mixture was concentrated under reduced pressure. Extracted, an appropriate amount of 1500 mL of dichloromethane was added, followed by successive washing with 800 mL of 10% sodium carbonate, 800 mL of 10% citric acid and 800 mL of saturated brine. The aqueous phase was back-extracted twice with 1000 mL of dichloromethane. The organic phases were combined, dried over anhydrous sodium sulfate for half an hour, filtered by suction, concentrated under reduced pressure and filtered through silica gel (200-300 mesh) column (EA:PE=1:10, 1:8, 1:5) to give 177 g of said 5-(tert-butyl)oxazole-4-ethyl formate as a yellow liquid with a yield of 113%.

2) Preparation of 5-(tert-butyl)-1H-imidazole-4-ethyl formate 157 g (796 mmol) of 5-(tert-butyl)-1H-oxazole-4-ethyl formate was added to 717 g (15.914 mmol) of formamide. The mixture was let stand in an oil bath at 180° C. and stirred under reflux for 30 hours, cooled to room temperature, extracted and added with 800 mL of 10% sodium carbonate. 500 mL of petroleum ether was added to extract and the organic phase was discarded. The obtained was then extracted three times with ethyl acetate (1000 mL*3). The organic phases were combined, washed twice with saturated brine (800 mL*2) and the aqueous phase was back-extracted twice with ethyl acetate (500 mL*2). The organic phases were combined, dried over anhydrous sodium sulfate, filtered by suction, concentrated under reduced pressure, pulpified, added with 1000 mL of water, stirred and filtered by suction. The filter cake was washed with water and dried in vacuo at 50° C. to give 71 g of said 5-(tert-butyl)-1H-imidazole-4-ethyl formate as a earthy-yellow solid with a yield of 45%.

3) Preparation of 5-(tert-butyl)-1H-imidazole-4-methanol 40 g (1054 mmol) of lithium aluminum hydride was added to 300 mL of dried tetrahydrofuran in a cold trap at −10° C. 70 g (357 mmol) of 5-(tert-butyl)-1H-imidazole-4-ethyl formate in 200 mL of tetrahydrofuran was slowly added dropwise to the turbid lithium aluminum hydride solution. The reaction was stirred at room temperature for 3 hours. Quenched by ice-water, the reaction solution was added dropwise into a measuring cup with an appropriate amount of ice. The mixture was filtered by suction, and the resulting filter cake was successively washed twice with water (1000 mL*2), twice with tetrahydrofuran (500 mL*2), twice with anhydrous ethanol (500 mL*2), concentrated under reduced pressure, and dehydrated by anhydrous ethanol to give 51 g of said 5-(tert-butyl)-1H-imidazole-4-methanol as a pale-yellow solid with a yield of 93%.

4) Preparation of 5-(tert-butyl)-1H-imidazole-4-carbaldehyde 50 g (324 mmol) of 5-(tert-butyl)-1H-imidazole-4-methanol was added to 500 mL of dichloromethane, followed by addition of 282 g (3242 mmol) of manganese dioxide. The reaction was stirred at room temperature for 24 hours. The mixture was filtered by suction and added with diatomite. The resulting filter cake was washed three times with anhydrous ethanol (500 mL*3) and concentrated under reduced pressure to give 43 g of said 5-(tert-butyl)-1H-imidazole-4-carbaldehyde as a pale-yellow solid with a yield of 87%.

5) Preparation of N,N-diacetylpiperazine-2,5-dione 50 g (438 mmol) of glycine anhydride was added to 179 g (1753 mmol) of acetic anhydride. The mixture was let stand in an oil bath at 155° C., stirred under reflux for 30 hours, concentrated under reduced pressure, dissolved in dichloromethane and filtered through diatomite and silica gel. The filter cake was rinsed with dichloromethane, concentrated under reduced pressure, dissolved in ethyl acetate at 70° C. and recrystallized to give 74 g of N,N-diacetylpiperazine-2,5-dione as a brown solid with a yield of 85%.

6) Preparation of (Z)-1-acetyl-3-[(5-(tert-butyl)-1H-imidazol-4-yl)methylene]piperazine-2,5-dione 1 g (6.5 mmol) of 5-(tert-butyl)-1H-imidazole-4-carbaldehyde was added to 7 mL of DMF, followed by addition of 2.59 g (13 mmol) of N,N-diacetylpiperazine-2,5-dione. The resulting solution was repeatedly exhausted under nitrogen for three times. 3.19 g (9.8 mmol) of cesium carbonate was added and the mixture was repeatedly exhausted under nitrogen for three times. The reaction was stirred at room temperature for 20 hours in the absence of light. The reaction solution was poured into ice-water (100 mL) and filtered by suction. The resulting filter cake was successively washed with water (100 mL*2) and an 8:1 mixture of petroleum ether and ethyl acetate (90 mL), then ultrasonically dispersed in ethanol and dichloromethane. The insolubles was filtered off and the resulting filtrate was concentrated under reduced pressure, dehydrated by anhydrous ethanol and pulpified with ethyl acetate (50 mL) to give 0.89 g of (Z)-1-acetyl-3-[(5-(tert-butyl)-1H-imidazol-4-yl)methylene]piperazine-2,5-dione as a brown-yellow solid with a yield of 46.9%.

7) Preparation of (3Z,6Z)-3-benzylidene-6-[(5-tert-butyl-1H-imidazol-4-yl)methylene]piperazine-2,5-dione 0.85 g (2.9 mmol) of (Z)-1-acetyl-3-[(5-(tert-butyl)-1H-imidazol-4-yl)methylene]piperazine-2,5-dione was added to DMF, followed by addition of 0.56 g (5.25 mmol) of benzaldehyde. The resulting solution was repeatedly exhausted under nitrogen for three times. 0.95 g (2.9 mmol) of cesium carbonate was added and the mixture was repeatedly exhausted under nitrogen for three times. The temperature was programmed to reach 80° C. and the reaction was stirred for 24 hours in the absence of light. The reaction solution was poured into ice-water (100 mL) and filtered by suction. The resulting filter cake was washed successively with water (100 mL*2) and an 8:1 mixture of petroleum ether and ethyl acetate (90 mL), then ultrasonically dispersed in ethanol (30 mL) and ethyl acetate (100 mL). The insolubles was filtered off and the resulting filtrate was concentrated under reduced pressure, dehydrated by anhydrous ethanol, dispersed with 50 mL of ethyl acetate, let stand at −30° C. overnight and filtered by suction. The resulting filter cake was washed with icy ethyl acetate (5 mL) to give 0.59 g of an α-crystalline form of (3Z,6Z)-3-benzylidene-6-[(5-tert-butyl-1H-imidazol-4-yl)methylene]piperazine-2,5-dione as a yellow powder solid with a yield of 60.1%.

Figure 10:
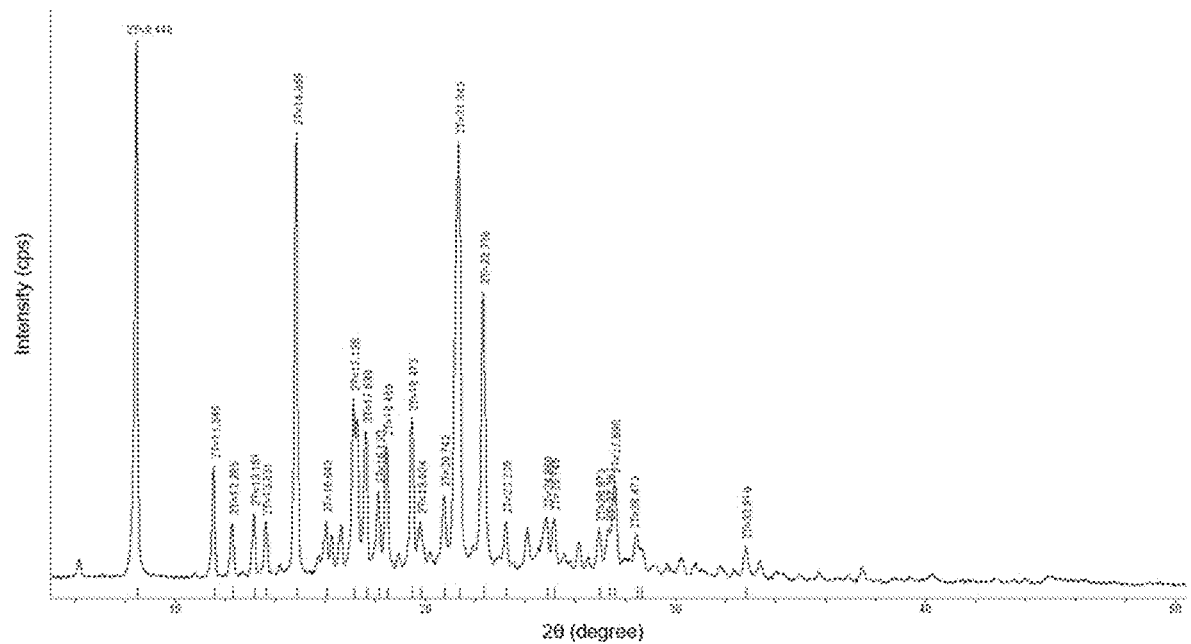
FIG. 10 shows an X-ray powder diffraction pattern of the a-crystalline form of (3Z,6Z)-3-benzylidene-6-[(5-tert-butyl-1H-imidazol-4-yl)methylene]piperazine-2,5-dione of the present invention.

$^1$H NMR (400 MHz, DMSO-d6) δ 12.31 (s, 1H), 12.22 (s, 1H), 10.00 (s, 1H), 7.84 (s, 1H), 7.52 (d, J=8 Hz, 2H), 7.39 (t, J=8 Hz, 2H), 7.32 (t, J=8 Hz, 1H), 6.86 (s, 1H), 6.73 (s, 1H), 1.37 (s, 9H); MS (ESI) m/z 338.1715 (M+H)$^+$ (calcd for $C_{19}H_{21}N_4O_2$ 338.1722). As shown in FIG. 10, the α-crystalline form has an X-ray powder diffraction pattern comprising characteristic peaks at 2θ angle of 8.446°, 11.546°, 12.285°, 13.161°, 14.855°, 16.043°, 16.647°, 17.136°, 17.639°, 18.130°, 18.459°, 19.473°, 19.804°, 20.742°, 21.343°, 22.338°, 23.235°, 24.868°, 25.145°, 27.596°.

Example 11

Figure 11:
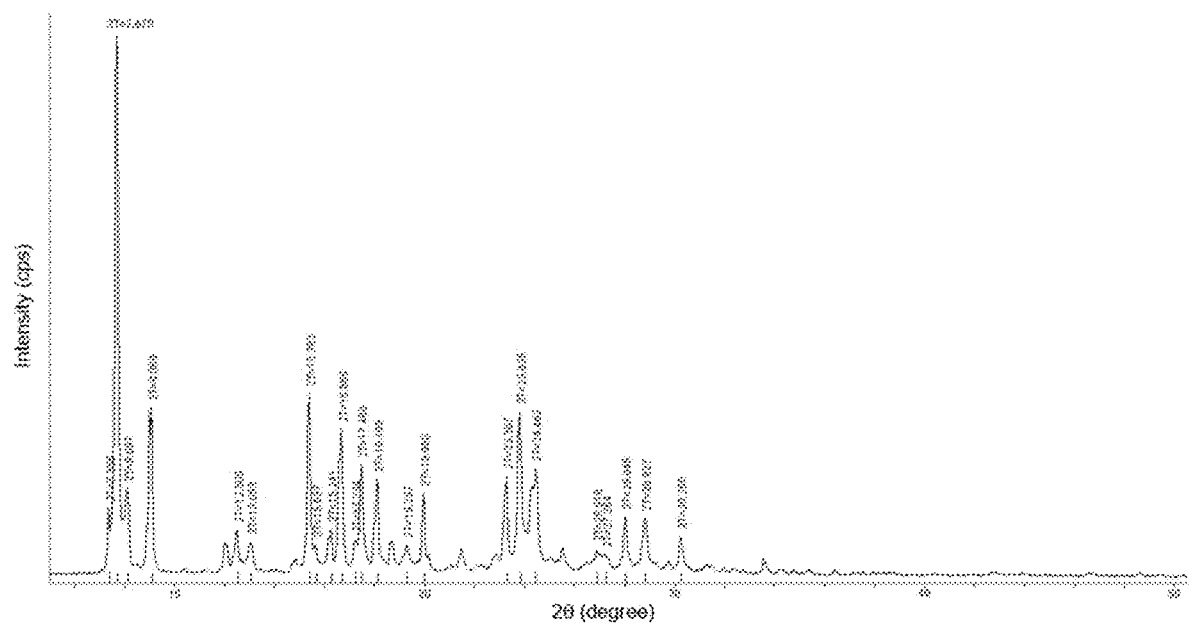
FIG. 11 shows an X-ray powder diffraction pattern of the b-crystalline form of (3Z,6Z)-3-benzylidene-6-[(5-tert-butyl-1H-imidazol-4-yl)methylene]piperazine-2,5-dione of the present invention.

Preparation of a b-Crystalline Form of (3Z,6Z)-3-benzylidene-6-[(5-tert-butyl-1H-imidazol-4-yl)methylene]piperazine-2,5-dione The specific preparation process comprises the following steps: weighing and dissolving said (3Z,6Z)-3-benzylidene-6-[(5-tert-butyl-1H-imidazol-4-yl)methylene]piperazine-2,5-dione (200 mg, 0.59 mmol) in a mixed solution of 20 mL of methanol and 0.1 mL of water at 70° C., filtering into a crystallization dish with its opening covered with a piece of plastic wrap membrane in which holes were made using a capillary with an outer diameter of 0.5 mm, letting stand to volatilize at room temperature in the absence of light to precipitate a b-crystalline form 72 hours later, filtering and drying to give 148 mg of a cubic solid with a yield of 74%. X-ray powder diffraction analysis shows that the obtained b-crystalline form exhibits characteristic absorption peaks at 2θ angle of 7.356°, 7.670°, 8.097°, 9.069°, 12.032°, 12.500°, 13.063°, 15.383°, 16.241°, 16.668°, 17.468°, 18.109°, 18.694°, 19.960°, 23.307°, 23.836°, 24.462°, 28.046°, 28.827°, 30.226°, the 2θ diffraction angle error is ±0.2°. The specific X-ray powder diffraction pattern is shown in FIG. 11. The melting point of obtained b-crystalline form is 264.0° C. to 264.9° C.

Figure 12:
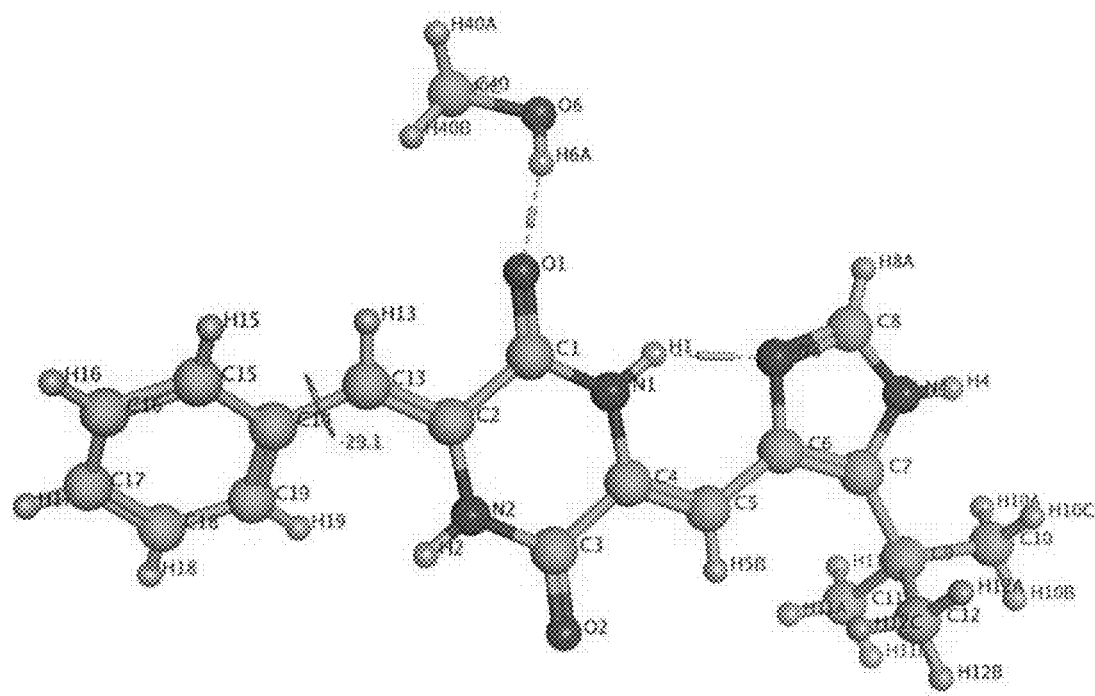
FIG. 12 shows an analytical structure diagram of X-ray single crystal diffraction of the b-crystalline form of (3Z,6Z)-3-benzylidene-6-[(5-tert-butyl-1H-imidazol-4-yl)methylene]piperazine-2,5-dione of the present invention.

The obtained b-crystalline form is determined as a single crystal in which one molecule of (3Z,6Z)-3-benzylidene-6-[(5-tert-butyl-1H-imidazol-4-yl)methylene]piperazine-2,5-dione is combined with one molecule of methanol. X-ray single crystal diffraction test is carried out on a Bruker X-ray single crystal diffractometer using Cu-Kα radiation (λ=1.54178 Å) at the temperature of 293K, with compound size set to be 0.45 mm×0.43 mm×0.32 mm and data collected at θ angle of 4.05 to 66.40 degrees. The test results of crystallographic parameters are shown in Table 12 below, and the analytical structure is shown in FIG. 12.

TABLE 12

| Crystallographic parameters | |
|---|---|
| Parameter | Test results |
| Empirical formula | $C_{20}H_{24}N_4O_3$ |
| Molecular weight | 368.43 |
| Crystal system | monoclinic |
| Space group | P2(1)/n |
| Unit cell dimensions | a = 14.6268(6) Å   α = 90 deg. |
|  | b = 17.0440(6) Å   β = 103.575(2) deg. |
|  | c = 16.0850(8) Å   γ = 90 deg. |
| Volume | 3898.0(3) Å$^3$ |
| Z, calculated density | 8, 1.256 Mg/m$^3$ |
| Absorption coefficient | 0.701 mm$^{-1}$ |
| Number of electrons in a unit cell | 1568 |
| Crystallite size | 0.45 × 0.43 × 0.32 mm |
| Limiting indices | −11 ≤ h ≤ 17, −20 ≤ k ≤ 9, −19 ≤ l ≤ 18 |
| Collected/unique diffraction data | 13871/6847 [R(int) = 0.0318] |
| Completeness to θ = 66.40 | 100.0% |
| Absorption correction parameters | Semi-empirical from equivalents |
| Max. and min transmission | 0.8067 and 0.7431 |
| Refinement method | Full-matrix least-squares on F$^2$ |
| Data/restraints/parameters | 6847/0/498 |
| Goodness-of-fit on F$^2$ | 1.018 |
| Final R indices | R1 = 0.0534, wR2 = 0.1362 |
| R indices (all data) | R1 = 0.0812, wR2 = 0.1541 |
| Light absorption coefficient | 0.00092(9) |
| Largest diff. peak and valley | 0.221 and −0.169 e · Å$^{-3}$ |

Example 12

Figure 13:
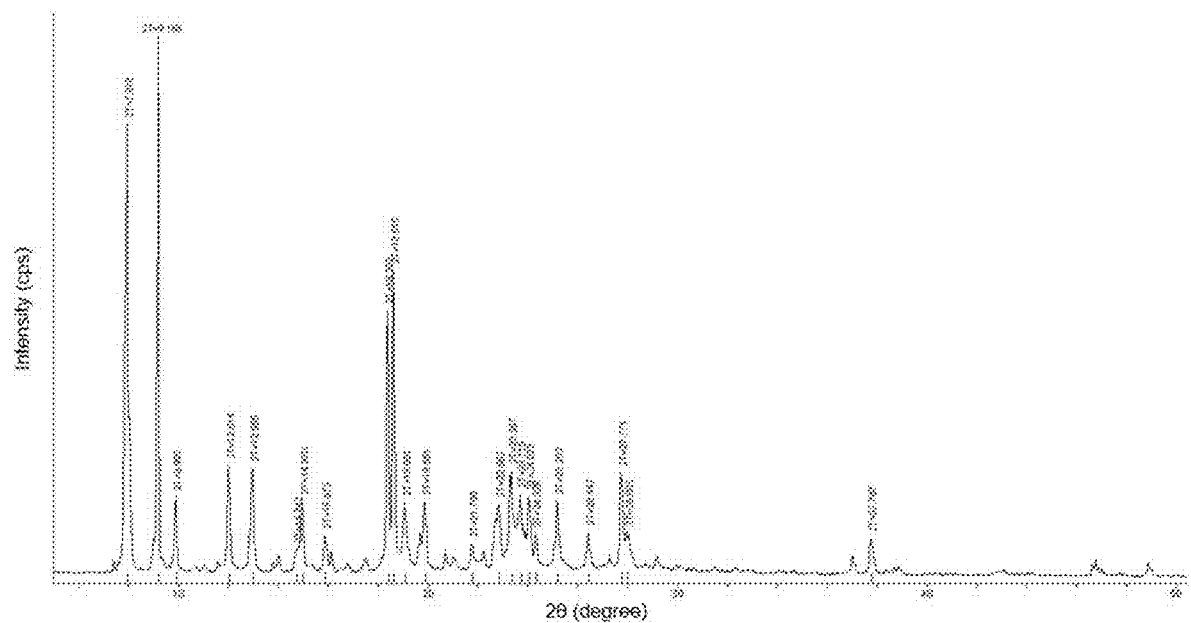
FIG. 13 shows an X-ray powder diffraction pattern of the c-crystalline form of (3Z,6Z)-3-benzylidene-6-[(5-tert-butyl-1H-imidazol-4-yl)methylene]piperazine-2,5-dione of the present invention.

Preparation of a c-Crystalline Form of (3Z,6Z)-3-benzylidene-6-[(5-tert-butyl-1H-imidazol-4-yl)methylene]piperazine-2,5-dione The specific preparation process comprises the following steps: weighing and dissolving said (3Z,6Z)-3-benzylidene-6-[(5-tert-butyl-1H-imidazol-4-yl)methylene]piperazine-2,5-dione (200 mg, 0.59 mmol) in a mixed solution of 20 mL of methanol and 0.8 mL of water at 68° C., filtering into a crystallization dish and inoculating with seed crystals, covering the opening of crystallization dish with a piece of plastic wrap membrane in which holes were made using a capillary with an outer diameter of 0.5 mm, letting stand to volatilize at room temperature in the absence of light to precipitate a c-crystalline form 72 hours later, filtering and drying to give 98 mg of a needle-like solid with a yield of 49%. X-ray powder diffraction analysis shows that the obtained c-crystalline form exhibits characteristic absorption peaks at 2θ angle of 7.918°, 9.168°, 9.905°, 12.014°, 12.985°, 14.970°, 15.873°, 18.382°, 18.616°, 19.081°, 19.881°, 22.862°, 23.367°, 23.719°, 24.073°, 25.203°, 26.447°, 27.771°, 37.787°, the 2θ diffraction angle error is ±0.2°. The X-ray powder diffraction pattern is shown in FIG. 13 and the melting point of obtained c-crystalline form is 263.2-264.0° C.

Figure 14:
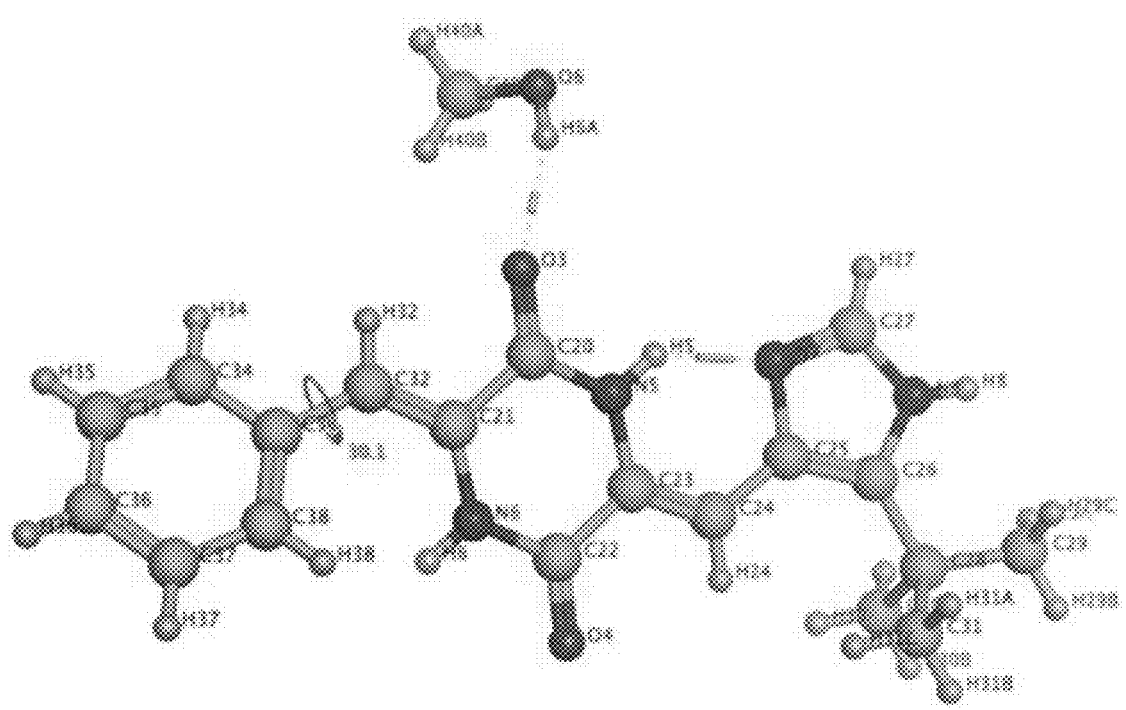
FIG. 14 shows an analytical structure diagram of X-ray single crystal diffraction of the c-crystalline form of (3Z,6Z)-3-benzylidene-6-[(5-tert-butyl-1H-imidazol-4-yl)methylene]piperazine-2,5-dione of the present invention.

The obtained c-crystalline form is a single crystal in which one molecule of (3Z,6Z)-3-benzylidene-6-[(5-tert-butyl-1H-imidazol-4-yl)methylene]piperazine-2,5-dione is combined with one molecule of methanol. X-ray single crystal diffraction test is carried out on a Bruker X-ray single crystal diffractometer using Cu-Kα radiation (λ=1.54178 Å) at the temperature of 293K, with compound size set to be 0.45 mm×0.30 mm×0.23 mm and data collected at θ angle of 4.05 to 66.40 degrees. The test results of crystallographic parameters are shown in Table 13 below, and the analytical structure is shown in FIG. 14.

TABLE 13

Crystallographic parameter table

| Parameter | Test results |
|---|---|
| Empirical formula | $C_{20}H_{24}N_4O_3$ |
| Molecular weight | 368.43 |
| Crystal system | monoclinic |
| Space group | P2(1)/n |
| Unit cell dimensions | a = 14.6218(11) Å    α = 90 deg. |
|  | b = 17.0401(11) Å    β = 103.604(2) deg. |
|  | c = 16.0771(13) Å    γ = 90 deg. |
| Volume | 3893.3(5) Å$^3$ |
| Z, calculated density | 8, 1.257 Mg/m$^3$ |
| Absorption coefficient | 0.702 mm$^{-1}$ |
| Number of electrons in a unit cell | 1568 |
| Crystallite size | 0.45 × 0.30 × 0.23 mm |
| Limiting indices | −17 ≤ h ≤ 13, −20 ≤ k ≤ 16, |
|  | −18 ≤ l ≤ 19 |
| Collected/unique diffraction data | 14326/6843 [R(int) = 0.0459] |
| Completeness to θ = 66.40 | 100.0% |
| Absorption correction parameters | Semi-empirical from equivalents |
| Max. and min transmission | 0.8552 and 0.7429 |
| Refinement method | Full-matrix least-squares on F$^2$ |
| Data/restraints/parameters | 6843/0/496 |
| Goodness-of-fit on F$^2$ | 1.017 |
| Final R indices | R1 = 0.0562, wR2 = 0.1340 |
| R indices (all data) | R1 = 0.1071, wR2 = 0.1635 |
| Light absorption coefficient | 0.00126(11) |
| Largest diff. peak and valley | 0.164 and −0.161 e · A$^{-3}$ |

The solvent molecules binding to the hydrogen bond in the conformation of obtained b—(as shown in FIG. 11) and c—(as shown in FIG. 14) crystalline forms of (3Z,6Z)-3-benzylidene-6-[(5-tert-butyl-1H-imidazol-4-yl)methylene]piperazine-2,5-dione are not limited to methanol, also include molecules that are prone to binding to the hydrogen bond in a carbonyl group such as other alkane saturated alcohols, unsaturated alcohols, alkane saturated amines or unsaturated amines.

Example 13

Figure 15:
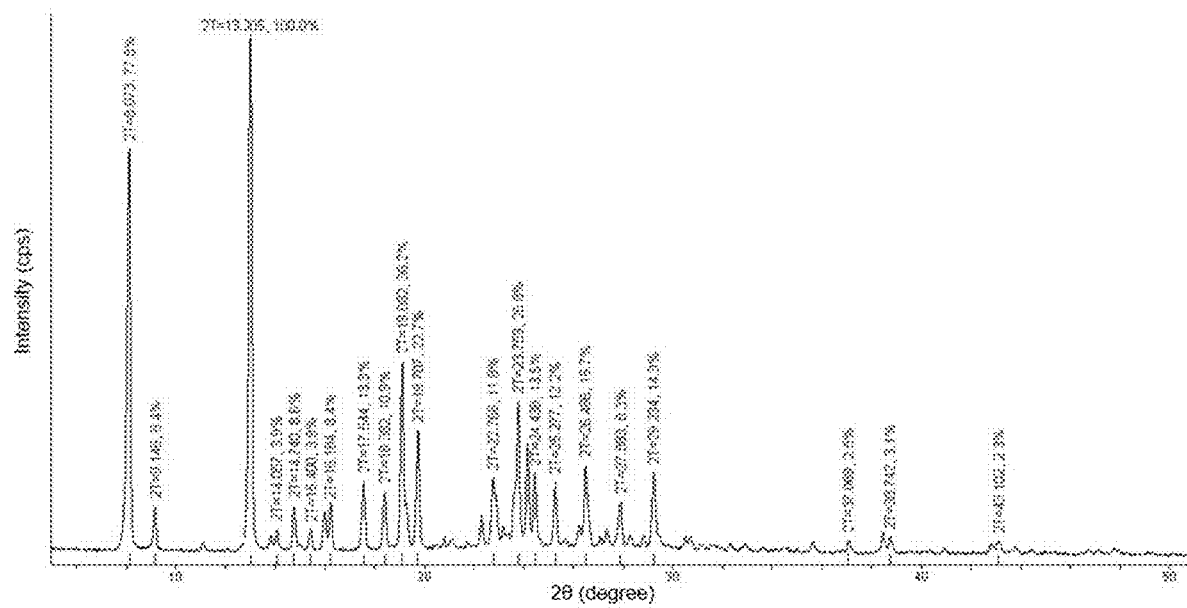
FIG. 15 shows an X-ray powder diffraction pattern of the d-crystalline form of (3Z,6Z)-3-benzylidene-6-[(5-tert-butyl-1H-imidazol-4-yl)methylene]piperazine-2,5-dione of the present invention.

Preparation of a d-Crystalline Form of (3Z,6Z)-3-benzylidene-6-[(5-tert-butyl-1H-imidazol-4-yl)methylene]piperazine-2,5-dione The specific preparation process comprises the following steps: weighing and dissolving said (3Z,6Z)-3-benzylidene-6-[(5-tert-butyl-1H-imidazol-4-yl)methylene]piperazine-2,5-dione solid (1.00 g, 2.96 mmol) in 60 mL of isopropanol at 80° C., filtering upon heating, letting the resulting filtrate stand at 80° C., adding 12 mL of water dropwise, stirring the resulting clear solution at room temperature to precipitate for 6 hours, filtering and drying to give 0.96 g of a yellow powdery crystalline solid with a yield of 91.61%. X-ray powder diffraction analysis shows that the obtained d-crystalline form exhibits characteristic absorption peaks at 2θ angle of 8.073°, 9.146°, 13.005°, 14.740°, 16.184°, 17.544°, 18.382°, 19.082°, 19.707°, 22.766°, 23.759°. 24.438°, 25.277°, 26.486°, 27.883°, 29.234°, the 2θ diffraction angle error is ±0.2°. The X-ray powder diffraction pattern is shown in FIG. 15, and the melting point of obtained d-crystalline form is 264.5° C. to 266.3° C.

Figure 16:
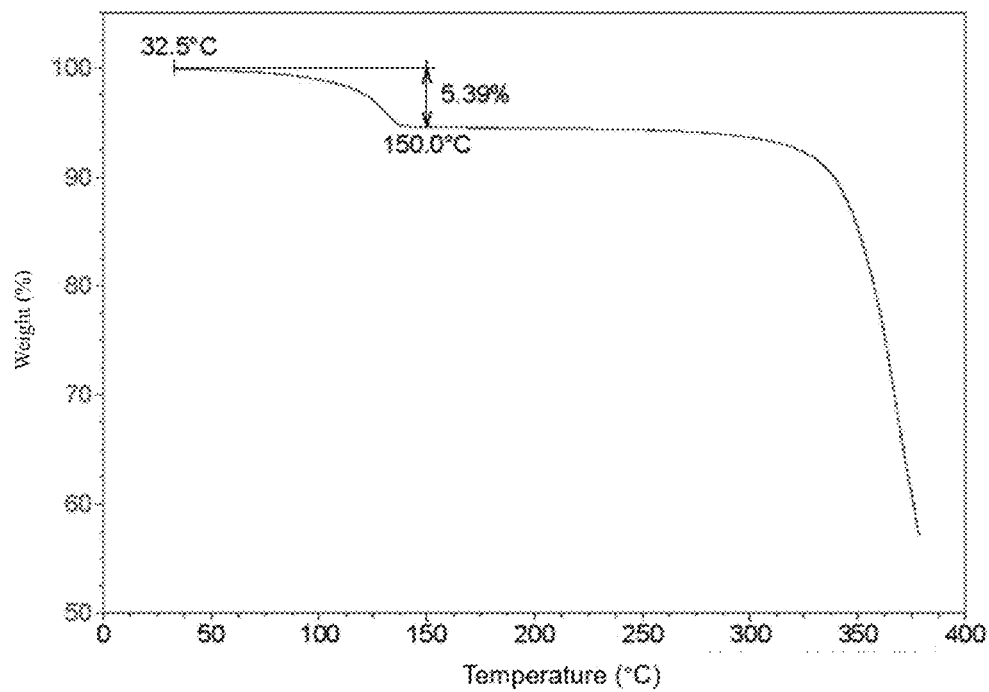
FIG. 16 shows a thermogravimetric analysis diagram of the d-crystalline form of (3Z,6Z)-3-benzylidene-6-[(5-tert-butyl-1H-imidazol-4-yl)methylene]piperazine-2,5-dione of the present invention.

The obtained d-crystalline form is a monohydrate of (3Z,6Z)-3-benzylidene-6-[(5-tert-butyl-1H-imidazol-4-yl) methylene]piperazine-2,5-dione, containing 5.326% water as determined by a Karl Fischer moisture meter. FIG. 16 shows the supporting data provided by a thermogravimetric analysis.

Table 14 shows data on powder XRD analysis of the a-, b-, c- and d-crystalline forms of (3Z,6Z)-3-benzylidene-6-[(5-tert-butyl-1H-imidazol-4-yl)methylene]piperazine-2,5-dione of the present invention.

TABLE 14

Data on powder XRD analysis of the a-, b-, c- and d-crystalline forms

| Content tested | a-crystalline form | b-crystalline form | c-crystalline form | d-crystalline form |
|---|---|---|---|---|
| Main characteristic absorption peaks of powder XRD | 8.446° | 7.356° | 7.918° | 8.073° |
|  | 11.546° | 7.670° | 9.168° | 9.146° |
|  | 12.285° | 8.097° | 9.905° | 13.005° |
|  | 13.161° | 9.069° | 12.014° | 14.740° |
|  | 14.855° | 12.032° | 12.985° | 16.184° |
|  | 16.043° | 12.500° | 14.970° | 17.544° |
|  | 16.647° | 13.063° | 15.873° | 18.382° |
|  | 17.136° | 15.383° | 18.382° | 19.082° |
|  | 17.639° | 16.241° | 18.616° | 19.707° |
|  | 18.130° | 16.668° | 19.081° | 22.766° |
|  | 18.459° | 17.468° | 19.881° | 23.759° |
|  | 19.473° | 18.109° | 22.862° | 24.438° |
|  | 19.804° | 18.694° | 23.367° | 25.277° |
|  | 20.742° | 19.960° | 23.719° | 26.486° |
|  | 21.343° | 23.307° | 24.073° | 27.883° |
|  | 22.338° | 23.836° | 25.203° | 29.234° |
|  | 23.235° | 24.462° | 26.447° |  |
|  | 24.868° | 28.046° | 27.771° |  |
|  | 25.145° | 28.827° | 37.787° |  |
|  | 27.596° | 30.226° |  |  |

Example 14

Preparation of a d-Crystalline Single Crystal of (3Z,6Z)-3-benzylidene-6-[(5-tert-butyl-1H-imidazol-4-yl)methylene]piperazine-2,5-dione The specific preparation process comprises the following steps: weighing and dissolving (3Z,6Z)-3-benzylidene-6-[(5-tert-butyl-1H-imidazol-4-yl)methylene]piperazine-2,5-dione (100 mg, 0.30 mmol) in a mixed solvent of 15 mL of anhydrous ethanol and 1 mL of water at 65° C., filtering into a crystallization dish with its opening covered with a piece of plastic wrap membrane in which 16 holes were made using a capillary with an outer diameter of 0.5 mm, letting stand to volatilize at 25° C. in the absence of light to precipitate a d-crystalline form 72 hours later, filtering and drying to give 52 mg of a long columnar solid with a yield of 49.5%. The melting point of obtained d-crystalline form is 264.2° C. to 265.3° C.

Figure 17:
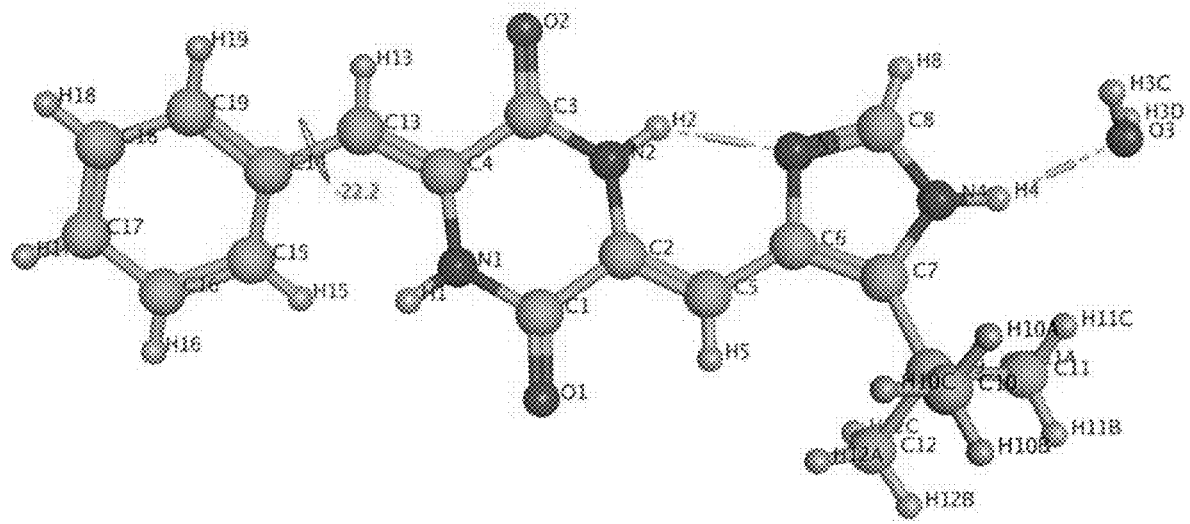
FIG. 17 shows an analytical structure diagram of X-ray single crystal diffraction of the d-crystalline form of (3Z,6Z)-3-benzylidene-6-[(5-tert-butyl-1H-imidazol-4-yl)methylene]piperazine-2,5-dione of the present invention.

The d-crystalline form is determined as a single crystal in which one molecule of (3Z,6Z)-3-benzylidene-6-[(5-tert-butyl-1H-imidazol-4-yl)methylene]piperazine-2,5-dione is combined with one molecule of water. X-ray single crystal diffraction test is carried out on a Bruker X-ray single crystal diffractometer using Cu-Kα radiation (λ=1.54178 Å) at the temperature of 293K, with compound size set to be 0.41 mm×0.40 mm×0.30 mm and data collected at θ angle of 4.06 to 66.19 degrees. The test results of crystallographic parameters are shown in Table 15 below, and the analytical structure is shown in FIG. 17.

TABLE 15

Crystallographic parameters

| Parameter | Test results |
| --- | --- |
| Empirical formula | $C_{19}H_{22}N_4O_3$ |
| Molecular weight | 354.41 |
| Crystal system | monoclinic |
| Space group | P2(1)/c |
| Unit cell dimensions | a = 9.7047(6) Å    α = 90 deg. |
|  | b = 8.5230(7) Å    β = 97.6060(10) deg. |
|  | c = 21.9790(15) Å  γ = 90 deg. |
| Volume | 1802.0(2) Å$^3$ |
| Z, calculated density | 4, 1.306 Mg/m$^3$ |
| Absorption coefficient | 0.738 mm$^{-1}$ |
| Number of electrons in a unit cell | 752 |
| Crystallite size | 0.41 × 0.40 × 0.30 mm |
| Limiting indices | −8 ≤ h ≤ 11, −9 ≤ k ≤ 10, −26 ≤ l ≤ 25 |
| Collected/unique diffraction data | 5932/3139 [R(int) = 0.0398] |
| Completeness to θ = 66.19 | 99.9% |
| Absorption correction parameters | Semi-empirical from equivalents |
| Max. and min transmission | 0.8089 and 0.7517 |
| Refinement method | Full-matrix least-squares on F$^2$ |
| Data/restraints/parameters | 3139/0/239 |
| Goodness-of-fit on F$^2$ | 1.069 |
| Final R indices | R1 = 0.0597, wR2 = 0.1506 |
| R indices (all data) | R1 = 0.0763, wR2 = 0.1626 |
| Light absorption coefficient | 0.0254(13) |
| Largest diff. peak and valley | 0.220 and −0.204 e · Å$^{-3}$ |

Example 15

Preparation of a Crude Product of (3Z,6Z)-3-benzylidene-6-[(5-tert-butyl-1H-imidazol-4-yl)deuteromethylene]piperazine-2,5-dione The specific preparation process includes the following steps:

1) Preparation of (Z)-1-acetyl-3-[(5-(tert-butyl)-1H-imidazol-4-yl)deuteromethylene]piperazine-2,5-dione 10.00 g (65.29 mmol) of 5-(tert-butyl)-1H-imidazol-4-deuteroformaldehyde was added to 50 mL of DMF, followed by addition of 25.88 g (130.59 mmol) of N,N-diacetylpiperazine-2,5-dione. The resulting solution was repeatedly exhausted under nitrogen for three times. 31.91 g (97.94 mmol) of cesium carbonate was added and the mixture was repeatedly exhausted under nitrogen for three times. The reaction was stirred at room temperature for 20 hours in the absence of light. The reaction solution was poured into ice-water (400 mL), filtered by suction, and the resulting filter cake was successively washed with water (200 mL*2) and a 8:1 mixture of petroleum ether and ethyl acetate (200 mL), then ultrasonically dispersed in ethanol and dichloromethane. The insolubles was filtered off and the resulting filtrate was concentrated under reduced pressure, dehydrated by anhydrous ethanol and then pulpified with ethyl acetate (250 mL) to give 8.96 g of (Z)-1-acetyl-3-[(5-(tert-butyl)-1H-imidazol-4-yl)deuteromethylene]piperazine-2,5-dione as a brown-yellow solid with a yield of 47.11%.

2) Preparation of a Crude Product of (3Z,6Z)-3-benzylidene-6-[(5-tert-butyl-1H-imidazol-4-yl)deuteromethylene]piperazine-2,5-dione 8.84 g (30.33 mmol) of (Z)-1-acetyl-3-[(5-(tert-butyl)-1H-imidazol-4-yl)deuteromethylene]piperazine-2,5-dione was added to 25 mL of DMF, followed by addition of 4.83 g (45.51 mmol) of benzaldehyde. The resulting solution was repeatedly exhausted under nitrogen for three times. 14.82 g (45.49 mmol) of cesium carbonate was added and the mixture was repeatedly exhausted under nitrogen for three times. The temperature was programmed to reach 50° C. and the reaction was stirred for 24 hours. The reaction solution was poured into ice-water (300 mL), filtered by suction, and the resulting filter cake was washed successively with water (200 mL*2) and an 8:1 mixture of petroleum ether and ethyl acetate (200 mL), then ultrasonically dispersed in ethanol (50 mL) and ethyl acetate (160 mL). The insolubles was filtered off and the resulting filtrate was concentrated under reduced pressure, dehydrated by anhydrous ethanol, ultrasonically dispersed in 150 mL of ethyl acetate, let stand at −30° C. overnight and filtered by suction. The filter cake was washed with 50 mL of icy ethyl acetate to give 6.66 g of a yellow-green solid with a yield of 65.09%.

Example 16

Preparation of a Monohydrate of (3Z,6Z)-3-benzylidene-6-[(5-tert-butyl-1H-imidazol-4-yl)deuteromethylene]piperazine-2,5-dione with High Purity

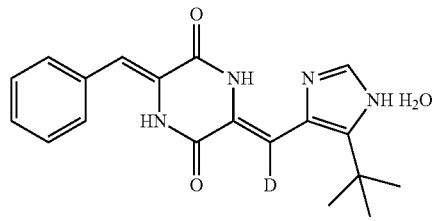

Figure 18:
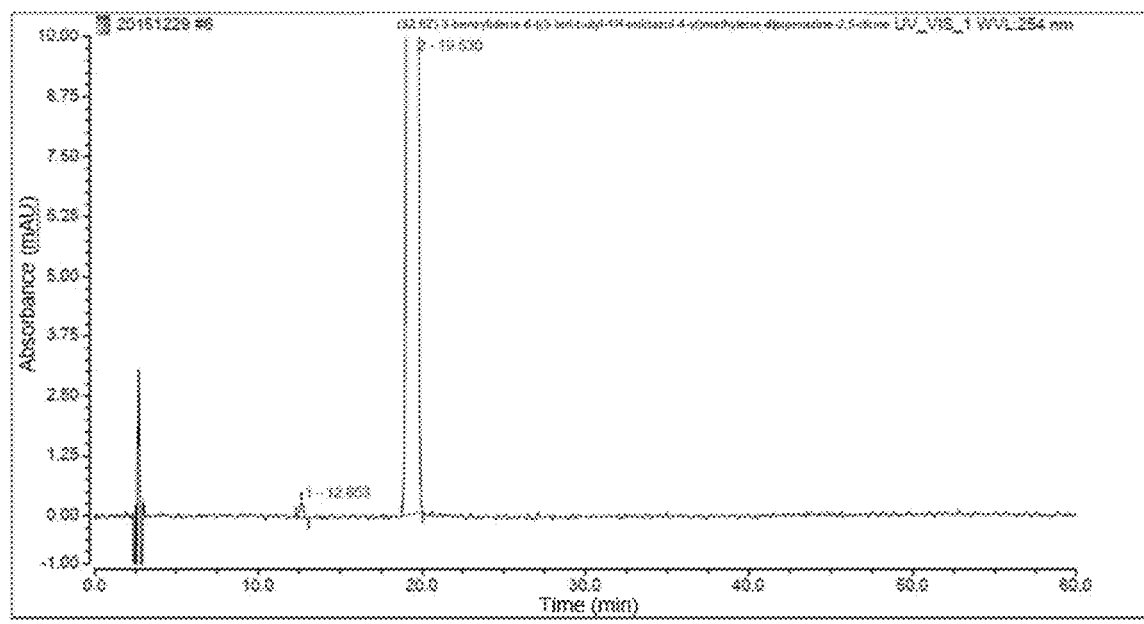
FIG. 18 shows a HPLC chromatogram of the monohydrate of (3Z,6Z)-3-benzylidene-6-[(5-tert-butyl-1H-imidazol-4-yl)deuteromethylene]piperazine-2,5-dione with high purity of the present invention at a wavelength of 254 nm.

2.0 g of the crude product disclosed in Example 1 was placed in a brown bottle, 125 mL of isopropanol was added under heating till said crude product completely dissolved. 50 mL of water was added resulting in no crystalline precipitation. The resulting solution was stirred and cooled to precipitate at room temperature and filtered by suction. The resulting filter cake was washed with a 1:1 mixture of isopropanol and water and dried to give 1.642 g of a yellow powdery solid with a yield of 78.13%. The product purity at 254 nm is 99.94%, wherein the content of isomer (3E,6Z)-3-benzylidene-6-[(5-tert-butyl-1H-imidazol-4-yl)deuteromethylene]piperazine-2,5-dione was 0.06%, see FIG. 18. $^1$H NMR (500 MHz, dmso) δ 12.22 (brs, 2H), 10.00 (brs, 1H), 7.82 (d, J=12.7 Hz, 1H), 7.51 (d, J=7.6 Hz, 2H), 7.40 (t, J=7.7 Hz, 2H), 7.30 (t, J=7.4 Hz, 1H), 6.73 (s, 1H), 1.37 (s, 9H). MS (ESI) m/z 338.1715 (M+H)+(calcd for $C_{19}H_{20}DN_4O_2$).

Figure 19:
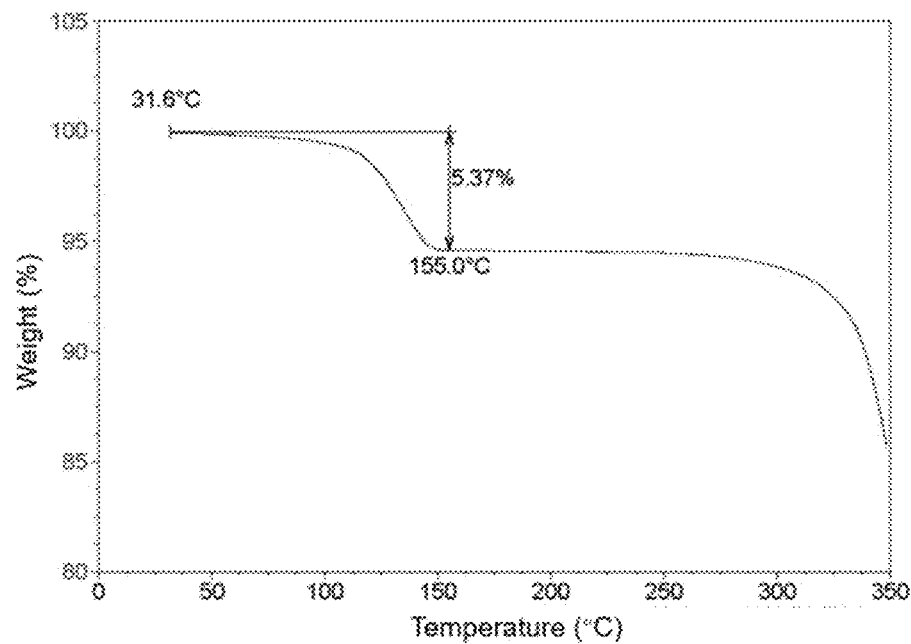
FIG. 19 shows a thermogravimetric analysis diagram of the monohydrate of (3Z,6Z)-3-benzylidene-6-[(5-tert-butyl-1H-imidazol-4-yl)deuteromethylene]piperazine-2,5-dione with high purity of the present invention.

The product obtained is a monohydrate of (3Z,6Z)-3-benzylidene-6-((5-tert-butyl-1H-imidazol-4-yl)deuteromethylene)piperazine-2,5-dione, containing 5.314% water. FIG. 19 shows the supporting data provided by a thermogravimetric analysis, wherein the element analysis is shown in Table 4 below.

Example 17

Preparation of a Crude Product of (3Z,6Z)-3-benzylidene-6-[(5-tert-butyl-1H-imidazol-4-yl)methylene]piperazine-2,5-dione The specific preparation process includes the following steps:

1) Preparation of 5-(tert-butyl)oxazole-4-ethyl formate 90 g (796 mmol) of ethyl isocyanoacetate was added to 1000 mL of tetrahydrofuran, followed by slow dropwise addition of 145 g (955 mmol) of DBU and dropwise addition of 178 g (955 mmol) of trimethylacetic anhydride. The reaction was stirred at room temperature for 48 hours. After the reaction was completed, the mixture was concentrated under reduced pressure. Extracted, an appropriate amount of 1500 mL of dichloromethane was added, followed by successive washing with 800 mL of 100% sodium carbonate, 800 mL of 10% citric acid and 800 mL of saturated brine. The aqueous phase was back-extracted twice with 1000 mL of dichloromethane. The organic phases were combined, dried over anhydrous sodium sulfate for half an hour, filtered by suction, concentrated under reduced pressure and filtered through silica gel (200-300 mesh) column (EA:PE=1:10, 1:8, 1:5) to give 177 g of 5-(tert-butyl)oxazole-4-ethyl formate as a yellow liquid with a yield of 113%.

2) Preparation of 5-(tert-butyl)-1H-imidazole-4-ethyl formate 157 g (796 mmol) of 5-(tert-butyl)-1H-oxazole-4-ethyl formate was added to 717 g (15.914 mmol) of formamide. The mixture was let stand in an oil bath at 180° C., stirred under reflux for 30 hours, cooled to room temperature, extracted and added with 800 mL of 10% sodium carbonate. 500 mL of petroleum ether was added to extract and the organic phase was discarded. Then extracted three times with ethyl acetate (1000 mL*3). The organic phases were combined and washed twice with saturated brine (800 mL*2). The aqueous phase was back-extracted twice with ethyl acetate (500 mL*2). The organic phases were combined and dried over anhydrous sodium sulfate, filtered by suction, concentrated under reduced pressure, pulpified, added with 1000 mL of water, stirred and filtered by suction. The resulting filter cake was washed with water and dried in vacuo at 50° C. to give 71 g of said 5-(tert-butyl)-1H-imidazole-4-ethyl formate as a earthy-yellow solid with a yield of 45%.

3) Preparation of 5-(tert-butyl)-1H-imidazole-4-methanol 40 g (1054 mmol) of lithium aluminum hydride was added to 300 mL of dried tetrahydrofuran in a cold trap at −10° C. 70 g (357 mmol) of 5-(tert-butyl)-1H-imidazole-4-ethyl formate dissolved in 200 mL of tetrahydrofuran was slowly added dropwise to the turbid solution of lithium aluminum hydride. The reaction was stirred at room temperature for 3 hours. Quenched by ice-water, the reaction solution was added dropwise into a measuring cup with an appropriate amount of ice, and filtered by suction. The resulting filter cake was successively washed twice with water (1000 mL*2), twice with tetrahydrofuran (500 mL*2), twice with anhydrous ethanol (500 mL*2), concentrated under reduced pressure, and dehydrated by anhydrous ethanol to give 51 g of said 5-(tert-butyl)-1H-imidazole-4-methanol as a pale-yellow solid with a yield of 93%.

4) Preparation of 5-(tert-butyl)-1H-imidazole-4-carbaldehyde 50 g (324 mmol) of 5-(tert-butyl)-1H-imidazole-4-methanol was added to 500 mL of dichloromethane, followed by addition of 282 g (3242 mmol) of manganese dioxide. The reaction was stirred at room temperature for 24 hours. The reaction mixture was filtered by suction and added with diatomite. The resulting filter cake was washed three times with anhydrous ethanol (500 mL*3) and concentrated under reduced pressure to give 43 g of said 5-(tert-butyl)-1H-imidazole-4-carbaldehyde as a pale-yellow solid with a yield of 87%.

5) Preparation of N,N-diacetylpiperazine-2,5-dione 50 g (438 mmol) of glycine anhydride was added to 179 g (1753 mmol) of acetic anhydride. The mixture was let stand in an oil bath at 155° C., stirred under reflux for 30 hours, concentrated under reduced pressure, dissolved in dichloromethane and filtered through diatomite and silica gel. The filter cake was rinsed with dichloromethane, concentrated under reduced pressure, dissolved in ethyl acetate at 70° C. and recrystallized to give 74 g of said N,N-diacetylpiperazine-2,5-dione as a brown solid with a yield of 85%.

6) Preparation of (Z)-1-acetyl-3-[(5-(tert-butyl)-1H-imidazol-4-yl)methylene]piperazine-2,5-dione 1 g (6.5 mmol) of 5-(tert-butyl)-1H-imidazole-4-carbaldehyde was added to 7 mL of DMF, followed by addition of 2.59 g (13 mmol) of N,N-diacetylpiperazine-2,5-dione. The resulting solution was repeatedly exhausted under nitrogen for three times. 3.19 g (9.8 mmol) of cesium carbonate was added and the mixture was repeatedly exhausted under nitrogen for three times. The reaction was stirred at room temperature for 20 hours in the absence of light. The reaction solution was poured into ice-water (100 mL) and filtered by suction. The resulting filter cake was successively washed with water (100 mL*2) and an 8:1 mixture of petroleum ether and ethyl acetate (90 mL), then ultrasonically dispersed in ethanol and dichloromethane. The insolubles was filtered off and the resulting filtrate was concentrated under reduced pressure, dehydrated with anhydrous ethanol, and pulpified with ethyl acetate (50 mL) to give 0.89 g of (Z)-1-acetyl-3-[(5-(tert-butyl)-1H-imidazol-4-yl)methylene]piperazine-2,5-dione as a brown-yellow solid with a yield of 46.9%.

7) Preparation of a Crude Product of (3Z,6Z)-3-benzylidene-6-[(5-tert-butyl-1H-imidazol-4-yl)methylene]piperazine-2,5-dione 0.85 g (2.9 mmol) of (Z)-1-acetyl-3-[(5-(tert-butyl)-1H-imidazol-4-yl)methylene]piperazine-2,5-dione was added to DMF, followed by addition of 0.56 g (5.25 mmol) of benzaldehyde. The resulting solution was repeatedly exhausted under nitrogen for three times. 0.95 g (2.9 mmol) of cesium carbonate was added and the mixture was repeatedly exhausted under nitrogen for three times. The temperature was programmed to reach 80° C. and the reaction was stirred for 24 hours in the absence of light. The reaction solution was poured into ice-water (100 mL) and filtered by suction. The resulting filter cake was washed successively with water (100 mL*2) and an 8:1 mixture of petroleum ether and ethyl acetate (90 mL), then untrasonically dispersed in ethanol (30 mL) and ethyl acetate (100 mL). The insolubles was filtered off and the resulting filtrate was concentrated under reduced pressure, dehydrated with anhydrous ethanol, dispersed in 50 mL of ethyl acetate, let stand at −30° C. overnight and filtered by sunction. The resulting filter cake was then washed with 5 mL of icy ethyl acetate to give 0.73 g of a crude product

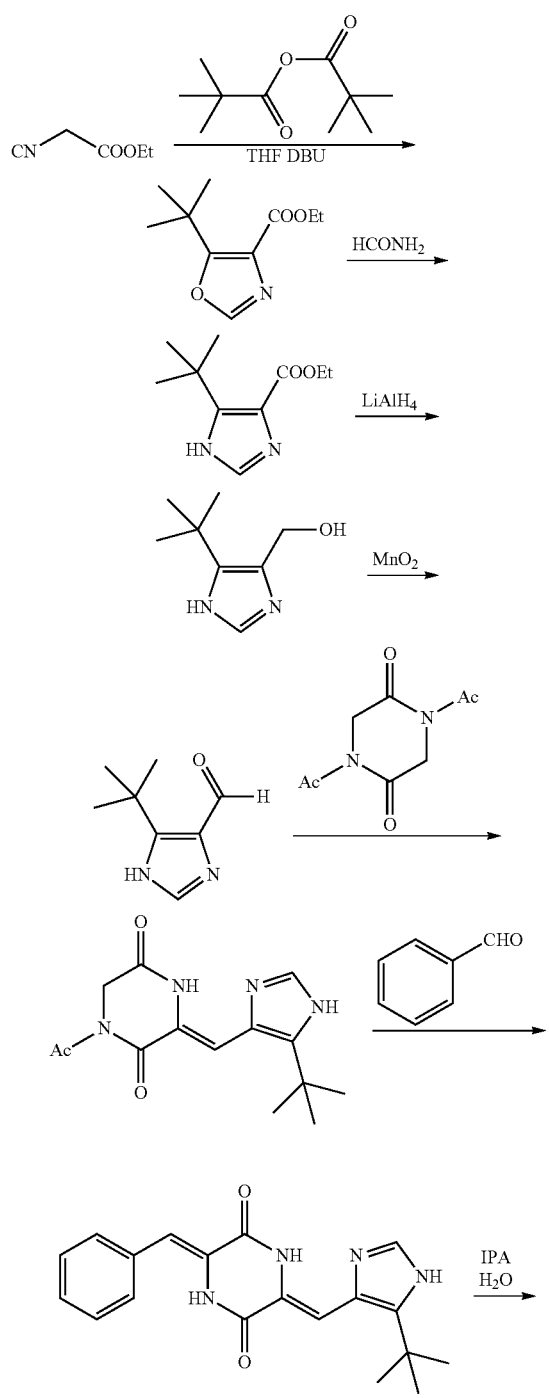

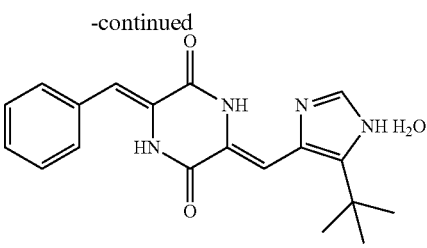

Example 18

Figure 20:
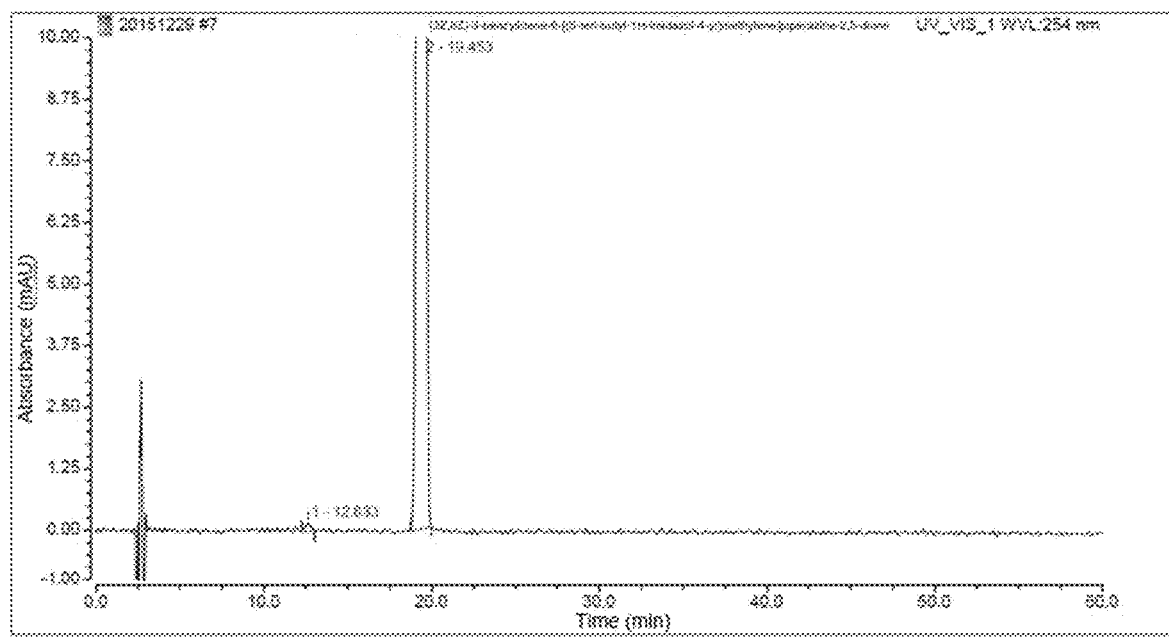
FIG. 20 shows a HPLC chromatogram of the monohydrate of (3Z,6Z)-3-benzylidene-6-[(5-tert-butyl-1H-imidazol-4-yl)methylene]piperazine-2,5-dione with high purity of the present invention at a wavelength of 254 nm.

Preparation of a Monohydrate of (3Z,6Z)-3-benzylidene-6-[(5-tert-butyl-1H-imidazol-4-yl)methylene]piperazine-2,5-dione with High Purity 0.73 g of said crude product was placed in a brown bottle, 45 mL of isopropanol was added under heating till said crude product completely dissolved. 18 mL of water was added resulting in no crystalline precipitation. The resulting solution was stirred and cooled to precipitate at room temperature and filtered by suction. The resulting filter cake was washed with a 1:1 mixture of isopropanol and water, and dried to give 0.59 g of a yellow powdery solid with a yield of 76.71%. The product purity was 99.91% at 254 nm, wherein the content of isomer (3E,6Z)-3-benzylidene-6-[(5-tert-butyl-1H-imidazol-4-yl)methylene]piperazine-2,5-dione was 0.09%, as shown in FIG. 20; $^1$H NMR (400 MHz, DMSO-d6) δ 12.31 (s, 1H), 12.22 (s, 1H), 10.00 (s, 1H), 7.84 (s, 1H), 7.52 (d, J=8 Hz, 2H), 7.39 (t, J=8 Hz, 2H), 7.32 (t, J=8 Hz, 1H), 6.86 (s, 1H), 6.73 (s, 1H), 1.37 (s, 9H); MS (ESI) m/z 337.1659 (M+H)$^+$ (calcd for $C_{19}H_{21}N_4O_2$).

Figure 21:
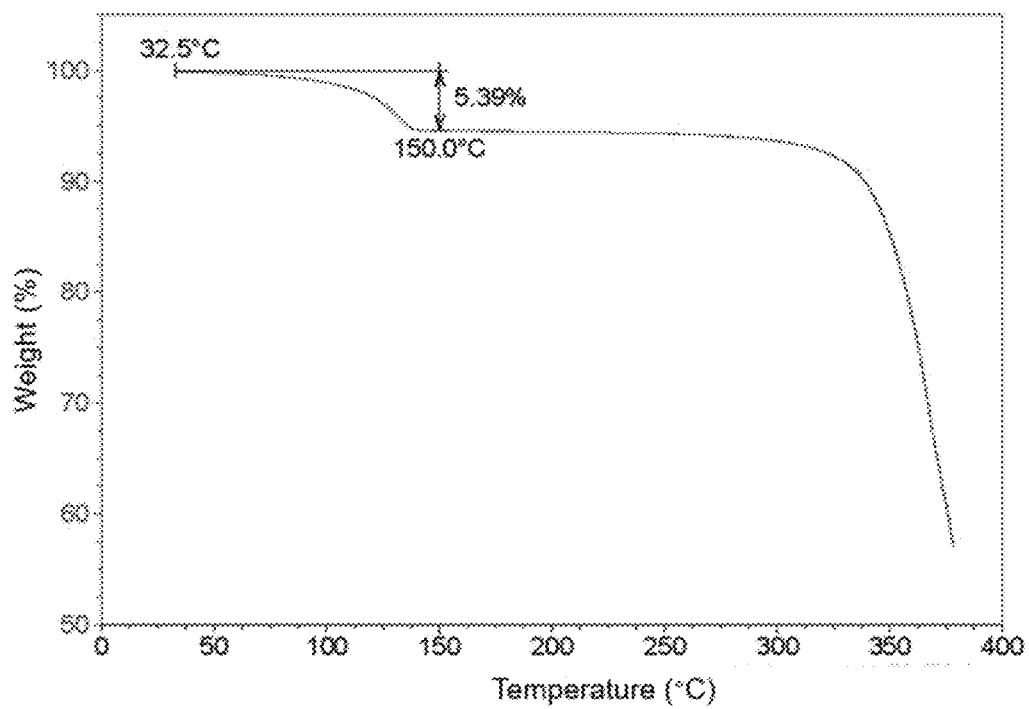
FIG. 21 shows a thermogravimetric analysis diagram of the monohydrate of (3Z,6Z)-3-benzylidene-6-[(5-tert-butyl-1H-imidazol-4-yl)methylene]piperazine-2,5-dione with high purity of the present invention.

The obtained product is a monohydrate of (3Z,6Z)-3-benzylidene-6-[(5-tert-butyl-1H-imidazol-4-yl)methylene]piperazine-2,5-dione, containing 5.326% water. FIG. 21 shows the supporting data provided by a thermogravimetric analysis.

Example 19

Preparation of 5-(tert-butyl)-1H-imidazole-4-ethyl formate intermediate 157 g (796 mmol) of 5-(tert-butyl)-1H-oxazole-4-ethyl formate was added to 717 g (15.91 mmol) of formamide. The mixture was let stand in an oil bath at 180° C., stirred under reflux for 30 hours, cooled to room temperature, extracted and added with 800 mL of 10% sodium carbonate. 500 mL of petroleum ether was added to extract and the organic phase was discarded. Then extracted three times with ethyl acetate (1000 mL*3). The organic phases were combined and washed twice with saturated brine (800 mL*2). The aqueous phase was back-extracted twice with ethyl acetate (500 mL*2). The organic phases were combined and dried over anhydrous sodium sulfate, filtered by suction, concentrated under reduced pressure, pulpified, added with 1000 mL water, stirred and filtered by suction. The resulting filter cake was washed with water, dried in vacuo at 50° C. to give 71 g of 5-(tert-butyl)-1H-imidazole-4-ethyl formate as a earthy-yellow solid with a yield of 45%.

Example 20

Preparation of N,N-diacetylpiperazine-2,5-dione intermediate 50 g (438 mmol) of glycine anhydride was added to 179 g (1753 mmol) of acetic anhydride. The mixture was let stand in an oil bath at 155° C., stirred under reflux for 30 hours, concentrated under reduced pressure, dissolved in dichloromethane and filtered through diatomite and silica gel. The resulting filter cake was rinsed with dichloromethane, concentrated under reduced pressure, dissolved in ethyl acetate at 70° C. and recrystallized to give 74 g of N,N-diacetylpiperazine-2,5-dione as a brown solid with a yield of 85%.

It should be noted that the preparation method provided by the present invention can not only be used for preparing a (3Z,6Z)-3-benzylidene-6-[(5-tert-butyl)-1H-imidazol-4-yl)deuteromethylene]piperazine-2,5-dione monohydrate with high purity and a (3Z,6Z)-3-benzylidene-6-[(5-tert-butyl)-1H-imidazol-4-yl)methylene]piperazine-2,5-dione monohydrate with high purity as disclosed in the embodiments, but also suitable for preparation and purification of all dehydrophenylahistin-like compounds with similar structures, which could be any dehydrophenylahistin-like compound disclosed in the patents of WO2001053290A1, WO2004054498A, WO2007035841A1 or WO2016192586A1, or derivatives of these compounds. Preferably, the dehydrophenylahistin-like compounds disclosed herein have a structure represented by the following formula:

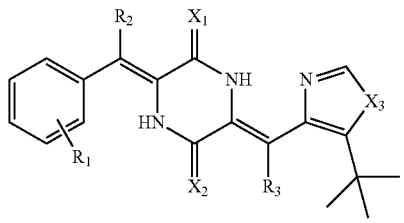

wherein $R_1$ is mono-substituted to penta-substituted substituent group on the benzene ring, which is independently selected from hydrogen, deuterium, 3-benzoylphenyl, 3-(4-methoxybenzoyl)phenyl, 3-(4-fluorobenzoyl)phenyl, halogen, hydroxy, methoxy, amino, phenyl, aminomethylphenyl, C1-C24 alkyl, C2-C24 alkenyl, C2-C24 alkynyl, arylalkyl, heterocycloarylalkyl, C1-C24 acyl, C1-C24 alkoxy, carboxy, carboxylate, acylamino, N-monosubstituted or N,N-disubstituted acylamino, sulfo, sulphonate, sulphonylamino, N-substituted sulphonylamino, alkoxy, arylalkoxy, alkylthio, cyano, amino, substituted amino, nitro, cycloalkyl, cycloalkenyl, aryl, substituted aryl, heterocycloaryl, aryloxy, aroyl, epoxy group, cycloacyl, arylthio, arylsulfonyl;

$R_2$ is hydrogen or deuterium, and $R_3$ is hydrogen or deuterium;

$X_1$ is oxygen or sulfur, and $X_2$ is oxygen or sulfur;

$X_3$ is —NH, oxygen or sulfur.

In the structure of dehydrophenylahistin-like compounds disclosed herein exists double bonds capable of forming a cis-trans isomer, and cis-trans isomerization is highly likely to occur under illumination condition. The method for preparing a dehydrophenylahistin-like compound with high purity disclosed in the claims of the present invention results from optimization of the purification methods for various similar compounds in the present invention, which significantly reduces the impurity content of isomers and yields an active compound with its purity higher than 99.9%.

Although detailed description of embodiments of the present invention has been described for the purpose of examplification, it is apparent to those skilled in the art that various changes and modifications to the preferred embodiments described herein can be made without departing from the spirit and scope of the present invention covered by the claims.

The invention claimed is:

1. A crystalline form of (3Z,6Z)-3-benzylidene-6-[(5-tert-butyl-1H-imidazol-4-yl)deuteromethylene]piperazine-2,5-dione as shown in Formula (I), wherein the crystalline form is only one crystalline form selected from the group consisting of α-crystalline form, β-crystalline form, γ-crystalline line form and δ-crystalline form, wherein, the α-crystalline form has at least three X-ray powder diffraction characteristic peaks at 2θ diffraction angle of 8.415°±0.2°, 11.512°±0.2°, 14.824°±0.2°, 17.087°±0.2°, 17.278°±0.2°, 19.461°±0.2°, 21.350°±0.2°, 22.344°±0.2° or 27.621°±0.2°;

the β-crystalline form has at least three X-ray powder diffraction characteristic peaks at 2θ diffraction angle of 7.629°±0.2°, 8.052°±0.2°, 12.967°±0.2°, 15.327°±0.2°, 16.195°±0.2°, 23.194°±0.2°, 23.760°±0.2°, 24.129°±0.2°, 24.419°±0.2°, 26.465°±0.2° or 29.213°±0.2°;

the γ-crystalline form has at least three X-ray powder diffraction characteristic peaks at 2θ diffraction angle of 8.075°±0.2°, 12.986°±0.2°, 16.217°±0.2°, 19.709°±0.2° or 24.441°±0.2°;

the δ-crystalline form has at least three X-ray powder diffraction characteristic peaks at 2θ diffraction angle of 8.075°±0.2°, 12.988°±0.2°, 16.201°±0.2°, 17.545°±0.2°, 19.084°±0.2°, 19.724°±0.2°, 23.710°±0.2°, 24.422°±0.2°, 26.485°±0.2° or 29.234°±0.2°;

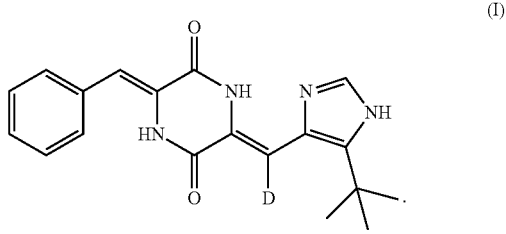 [SMILES: [2H]/C(c1nc[nH]c1C(C)(C)C)=c1/[nH]c(=O)/c(=C/c2ccccc2)[nH]c1=O]

(I)

2. The crystalline form according to claim 1, wherein the X-ray powder diffraction pattern of the α-crystalline form is consistent with FIG. 1.

3. The crystalline form according to claim 1, wherein the X-ray powder diffraction pattern of the β-crystalline form is consistent with FIG. 2.

4. The crystalline form according to claim 1, wherein the X-ray powder diffraction pattern of the γ-crystalline form is consistent with FIG. 4.

5. The crystalline form according to claim 1, wherein the δ-crystalline form is a single crystal which is a monohydrate of (3Z,6Z)-3-benzylidene-6-[(5-tert-butyl-1H-imidazol-4-yl)deuteromethylene]piperazine-2,5-dione.

6. The crystalline form according to claim 1, wherein the X-ray powder diffraction pattern of the δ-crystalline form is consistent with FIG. 6.

7. The crystalline form according to claim 6, wherein the δ-crystalline form is cultivated into a single crystal which is determined by X-ray single crystal diffraction analysis as monoclinic single crystal and has a space group of P2(1)/n and whose analytical structure is consistent with FIG. 7, and the melting point is 263° C. to 267° C.

8. A method of preparing the δ-crystalline form claim 1, wherein the method of preparing the δ-crystalline form comprises the following steps:

using a mixed solvent of water and an organic solvent as crystallization solvent, wherein the organic solvent is selected from at least one of an alkane saturated alcohol, an unsaturated alcohol, an alkane saturated amine and an unsaturated amine;

recrystallizing (3Z,6Z)-3-benzylidene-6-[(5-tert-butyl-1H-imidazol-4-yl)deuteromethylene]piperazine-2,5-dione in the mixed solvent, cooling and stirring, and precipitating to obtain the δ-crystalline form.

9. The method according to claim 8, wherein the composition of the organic solvent and the mixed solvent is any one of the followings:

1) the organic solvent is methanol, and the mixed solvent comprises water and methanol with a volume ratio of $V_{water}:V_{methanol}$ ranging from 1:100 to 10:1; or 2) the organic solvent is ethanol, and the mixed solvent comprises water and ethanol with a volume ratio of $V_{water}:V_{ethanol}$ ranging from 1:100 to 10:1; or 3) the organic solvent is isopropanol, and the mixed solvent comprises water and isopropanol with a volume ratio of $V_{water}:V_{isoproanol}$ ranging from 1:100 to 10:1.

10. The method according to claim 8, comprising the following steps: placing (3Z,6Z)-3-benzylidene-6-[(5-tert-butyl-1H-imidazol-4-yl)deuteromethylene]piperazine-2,5-dione in a reaction vessel in the absence of light, adding isopropanol as solvent and heating till dissolving completely, then adding water with a volume ratio of $V_{water}$ to $V_{isopropanol}$ ranging from 1:100 to 1:1, keeping at −10° C. to 30° C., stirring and cooling to precipitate, suction filtering, washing and drying to obtain the δ-crystalline form.

11. The method according to claim 10, wherein the volume ratio of $V_{water}$ to $V_{isopropanol}$ is 2:5, preferably keeping at −5° C. to 10° C., stirring and cooling to precipitate.

12. A method for treating a tumor in a subject in need thereof, comprising administering an effective amount of the crystalline form according to claim 1 to the subject.

* * * * *